US012417237B2

(12) United States Patent
Mitchell et al.

(10) Patent No.: US 12,417,237 B2
(45) Date of Patent: Sep. 16, 2025

(54) DETERMINING RELATIONSHIPS OF HISTORICAL DATA RECORDS

(71) Applicant: Ancestry.com Operations Inc., Lehi, UT (US)

(72) Inventors: Anne Gillespie Mitchell, Fremont, CA (US); Kaleb Benjamin White, Herriman, UT (US); Matt Landon Rasmussen, Orem, UT (US); Rey Robert Furner, Lindon, UT (US); Douglas Garry Earl, Orem, UT (US); Bryce Damon Ririe, Highland, UT (US); Donald Bernard Curtis, Highland, UT (US)

(73) Assignee: Ancestry.com Operations Inc., Lehi, UT (US)

( * ) Notice: Subject to any disclaimer, the term of this patent is extended or adjusted under 35 U.S.C. 154(b) by 0 days.

(21) Appl. No.: 18/108,015

(22) Filed: Feb. 10, 2023

(65) Prior Publication Data
US 2023/0252052 A1 Aug. 10, 2023

Related U.S. Application Data

(60) Provisional application No. 63/308,659, filed on Feb. 10, 2022.

(51) Int. Cl.
*G06F 16/28* (2019.01)
*A61B 17/00* (2006.01)
(Continued)

(52) U.S. Cl.
CPC ............ *G06F 16/285* (2019.01); *A61B 17/00* (2013.01); *A61B 34/25* (2016.02); *A61B 34/30* (2016.02);
(Continued)

(58) Field of Classification Search
CPC ............................ G06F 16/285; G06F 16/248
See application file for complete search history.

(56) References Cited

U.S. PATENT DOCUMENTS

2010/0049736 A1* 2/2010 Rolls .................... G06F 16/212
707/E17.055
2011/0246494 A1 10/2011 Adair et al.
(Continued)

OTHER PUBLICATIONS

Rolls et al., WO 2008/053493 A2, PCT /IL2007/001341, Nov. 4, 2007 (Year: 2007).*
(Continued)

*Primary Examiner* — Mohsen Almani
(74) *Attorney, Agent, or Firm* — Keller Preece PLLC

(57) ABSTRACT

A computing server may receive genealogical records that include historical records of deceased individuals. The computing server may normalize the genealogical records into normalized genealogical records. Normalizing the genealogical records may include converting a text string of a genealogical record into a standardized format. The computing server may stitch the normalized genealogical records into a plurality of clusters. Each cluster corresponds to an individual and includes one or more genealogical records associated with the individual. The computing server may identify a life-event record that is commonly associated with a subset of clusters, the life-event record indicating that a plurality of deceased individuals are connected through a non-familial relationship in a life event documented by the life-event record. The computing server may cause a graphical user interface to display a representation of a historical network among the plurality of deceased individuals that are connected through the non-familial relationship.

20 Claims, 14 Drawing Sheets

(51) Int. Cl.
  *A61B 34/00* (2016.01)
  *A61B 34/30* (2016.01)
  *A61B 90/00* (2016.01)
  *A61B 90/25* (2016.01)
  *G06F 16/24* (2019.01)
  *G06F 16/248* (2019.01)

(52) U.S. Cl.
  CPC .............. *A61B 90/06* (2016.02); *A61B 90/25* (2016.02); *G06F 16/248* (2019.01); *A61B 2017/00203* (2013.01); *A61B 2090/067* (2016.02)

(56) References Cited

U.S. PATENT DOCUMENTS

2016/0179806 A1   6/2016   Mortensen et al.
2021/0043319 A1*  2/2021   Lequeux ............. G06F 16/2272

OTHER PUBLICATIONS

Kennard, Douglas J., William B. Lund, and Bryan S. Morse. "Improving historical research by linking digital library information to a global genealogical database." Proceedings of the 9th ACM/IEEE-CS joint conference on Digital libraries. 2009. (Year: 2009).*

Kononenko, Oleksii, et al. "Mining modern repositories with elasticsearch." Proceedings of the 11th working conference on mining software repositories. 2014. (Year: 2014).*

Allgaier et al., WO 2015/195959 A1, PCT /US2015/036496, Jun. 18, 2015 (Year: 2015).*

Peleg et al., WO 2022/015730 A1, PCT/US2021/041428, Jul. 13, 2021 (Year: 2021).*

Dan Rolls et al., WO 2009/010948 A1, PCT /IL2007 /000909, Jul. 18, 2007 (Year: 2007).*

Wetherell, Charles. "Historical social network analysis." International review of social history 43.S6 (1998): 125-144. (Year: 1998).*

Wilson, D. Randall. "Beyond probabilistic record linkage: Using neural networks and complex features to improve genealogical record linkage." The 2011 international joint conference on neural networks. IEEE, 2011. (Year: 2011).*

Kennard, Douglas J., Andrew M. Kent, and William A. Barrett. "Linking the past: discovering historical social networks from documents and linking to a genealogical database." Proceedings of the 2011 Workshop on Historical Document Imaging and Processing. 2011. (Year: 2011).*

Folkman, T. et al. "GenERes: A Genealogical Entity Resolution System." Abstract, 2018 IEEE International Conference on Data Mining Workshops (ICDMW), Nov. 17-20, 2018, pp. 1.

PCT International Search Report and Written Opinion, PCT Application No. PCT/IB2023/051194, Apr. 17, 2023, nine pages.

* cited by examiner

Maine 17th Volunteer Infantry

OVERVIEW TIMELINE COMPANIES SOLDIERS IMAGES

Lorem ipsum dolor sit amet, consectetur sit amet adipiscing elit. Aliquam faucibus quis quam eget aliquet. Phasellus egestas tellus in interdum suscipit. Etiam accumsan dui tellus, sit amet...

Search for a Solider in the 55th North Carolina Infantry... 🔍

NOTABLE BATTLES

| ✕ Battle | ✕ Battle | ✕ Battle | ✕ Battle |
|---|---|---|---|
| Battle of Fredericksburg | Battle of Chancellorsville | Battle of Gettysburg | Battle of Wilderness |

◉ VIEW COMPANY A TIMELINE

COMMANDER LIST

Abernathey, Sidney
SOLDIER
Lorem: Ipsum Dolor Sit
Ipsum: Amet Consectuter
Dolor Sit: Adispicing Elit

Abernathey, Sidney
SOLDIER
Lorem: Ipsum Dolor Sit
Ipsum: Amet Consectuter
Dolor Sit: Adispicing Elit

---

Search for a Solider in... 🔍

FIELD OFFICERS

THUMBNAIL — General J.R. Davis (1861-1865)

THUMBNAIL — Lieutenant Colonel Alfred H. Belo (1861-1863)

THUMBNAIL — Lieutenant Colonel Abner S. Colloway (1862-1865)

THUMBNAIL — Lieutenant Colonel Maurice T. Smith (1861-1863)

THUMBNAIL — Major James S. Whitehead (1863-1865)

COMPANIES

Company A
Company B "Nickname"
Company C
Company D
Company E "Nickname"
Company F
Company G
Company H
Company I
Company J

*FIG. 6*

RETURN TO 55 NORTH CAROLINA INFANTRY

OVERVIEW TIMELINE SOLDIERS IMAGES

Company A mustered in on May 2nd, 1862.

Search for a Solider in the 55th North Carolina Infantry... 🔍

NOTABLE BATTLES

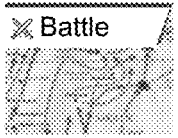 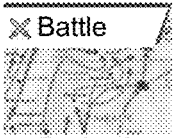 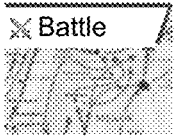 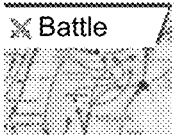

Battle of Gettysburg | Battle of Williamsport | Battle of Wilderness | Battle of Globe Tavern

[ VIEW COMPANY A TIMELINE ]

COMPANY A FACTS

Lorem ipsum dolor sit amet, consectetur adipiscing elit. Praesent urna risus, auctor id neque eu, ultrices suscipit metus. Quisque sit amet velit posuere, facilisis magna vitae, imperdiet quan.

Company A Casualties/POWs

0 ——— 77 ——— 154

⚰ 45 Died in War                 ✦ 51 Wounded
⚰ 50 Died in Regiment       ✦ 53 Prisoners of War Company A Age

16 ——— 23 ——— 63

● Youngest Soldier: 17 Hadley, JC   ● Oldest Soldier: 62 Short, Richard
◆ Median Enlistment Age: 26              ◆ Average Enlistment Age: 28.1

Company A Locations

⚐ First Enlistment Place: Pitt County, NC, 26 April, 1861 (1 Soldier)
⚐ Most Common Enlistment Place: Wilson County, NC (80 Soldiers)
⚐ Most Common Residence 1862: Wilson County, NC (92 Soldiers)
   Most Common Enlistment Date: 29 April, 1862 (19 Soldiers)

Search for a Solider in... 🔍

COMPANY A LEADERS

THUMBNAIL  Captain
           J. Doe
           (1861-1865)

THUMBNAIL  Lieutenant
           John Smith
           (1861-1863)

THUMBNAIL  Sergeant Major
           Abner S. Calloway
           (1862-1865)

NOTABLE SOLDIERS

THUMBNAIL  Corporal
           J. Doe
           (1861-1865)

THUMBNAIL  Private
           John Smith
           (1861-1863)

THUMBNAIL  Private
           Abner S. Calloway
           (1862-1865)

903   FPO      First Middle Lastname  ✏EDIT          🖨🔖↗         Save to Ancestry
      Soldier  Civil War (Union) · Branch · Regiment · Company · Rank
      Thumbnail

906   FACTS  STORIES  GALLERY  CONNECTIONS

[  ] [  ] [  ]
      TIMELINE                        ✏EDIT  +ADD    View Additional Images

• BIRTH – 22 FEB 1830                          SUPPORTING RECORDS
        Cityname, State
        Lorem Ipsum Dolor                            [sm thumb] Record Name
        Sit Amet consectutuer                        [sm thumb] Record Name
        ┌──────────┬────────────────────────┐        [sm thumb] Record Name
        │ FPO Birth│ Name of Birth Record↗  │        [sm thumb] Record Name
        │ Record   │ ⇒ Ancestry Record      │        [sm thumb] Record Name
        │ Thumb    │                        │        [sm thumb] Record Name
        └──────────┴────────────────────────┘        [sm thumb] Record Name
        4 More Records: 3 Ancestry Records, 1 Fold3 Record  ⌄

• 1861 – 1865 Civil War (Union) · Ages 31-35   ANCESTRY TREES
        REGIMENT                                     [sm thumb] Lorem Family Tree
        Regiment Name                                [sm thumb] Ipsum Family Tree  — 907
        ┌──────────┬────────────────────────┐        [sm thumb] Dolor Sit Amet
        │ FPO      │ Regiment Name          │                   Family Tree
        │ Regiment │ ⚔ Fold3 War Story      │
        │ Thumb    │                        │        PARTNERS
        └──────────┴────────────────────────┘
        STATE                                        TOGETHER WE SERVED
        State
        COMPANY                                      PUBLICATIONS
        Company Name
        ┌──────────┬────────────────────────┐        Publication Name
        │ FPO      │ Company Name           │        Title Name
        │ Company  │ ⚔ Fold3 War Story      │        Title Name
        │ Thumb    │                        │
        └──────────┴────────────────────────┘        Owner: Fold3_Team
        BRANCH                                       Created: 30 October 2013
        US Army                                      Modified: 30 October 2013
                                                     View Count: 60 (Recent: 2)
      • ENLISTMENT · 1862 · Age 32
        Cityname, State                              Source information: Lorem ipsum
        ┌──────────┬────────────────────────┐        dolor sit amet, consectetur
        │ FPO Military│ Name of Military Record│      adipiscing elit. Etiam molestie
        │ Record    │ ⚔ Fold3 War Story      │       viverra mattis. Sed diam ex,...
        │ Thumb     │                        │
        └──────────┴────────────────────────┘        [ CREATE A NEW MEMORIAL ]
        Added by: Username
        1 More Record: 1 Newspaper.com Record  ⌄

• BATTLE OF PLACE · 1863 · Age 33
        Cityname, State
        ┌──────────┬────────────────────────┐
        │ FPO      │ Battle Name            │
        │ Battle   │ ⚔ Fold3 War Story      │
        │ Thumb    │                        │
        └──────────┴────────────────────────┘
        1 More Record: 1 Fold3 Record  ⌄

⚔ Possible Pension Records

| | First Middle Lastname [EDIT] | | | Save to Ancestry |
|---|---|---|---|---|
| FPO Soldier Thumbnail | Civil War (Union) · Branch · Regiment · Company · Rank | | | |

FACTS    STORIES    GALLERY    CONNECTIONS

ALL FACT SOURCES

| | Record | Events | Title | Source Website |
|---|---|---|---|---|
| sm thumb | Record Name | Birth | Lorem Ipsum | Ancestry |
| sm thumb | Record Name | Lorem, Ipsum, Dolor | Lorem Ipsum | Ancestry |
| sm thumb | Record Name | Lorem, Ipsum, Dolor | Dolor Sit Amet | Ancestry |
| sm thumb | Record Name | Lorem, Ipsum, Dolor | Consectutuer Adispicing | Ancestry |
| sm thumb | Record Name | Military Service · Civial War (1861-1865) | Integer Laoreet | Fold3 |
| sm thumb | Record Name | Lorem, Ipsum, Dolor | Integer Laoreet | Fold3 |
| sm thumb | Record Name | Death | The Times | Newspapers.com |
| sm thumb | Record Name | Burial | Cemetary | Find a Grave |

MEMORIALS                                                                 [EDIT] [+ ADD]

| THUMBNAIL | Firstname Last Relationship | THUMBNAIL | Firstname Last Relationship | THUMBNAIL | Firstname Last Relationship |
|---|---|---|---|---|---|
| THUMBNAIL | Firstname Last Relationship Added by: Username | THUMBNAIL | Firstname Last Relationship Added by: Username | | |

RELATED (FOLD3 MEMBERS)

| THUMBNAIL | Firstname Last Relationship | THUMBNAIL | Firstname Last Relationship |
|---|---|---|---|

[+ ADD A NEW CONNECTION]  [+ I'M RELATED]

Add a Fact ✕

Import Facts | Add Facts Manually

Fact Type [Select ▼] [Birth Place]
Fact [Cityname, State]

Facts that will be added:

BIRTH DATE
22 FEB 1830 🗑 ✏ [+ ADD A SOURCE]
　　　　　　　　　Source Title Here 🗑 ✏

BIRTH PLACE
Cityname, State 🗑 ✏ [+ ADD A SOURCE]

LOREM IPSUM
Dolor Sit 🗑 ✏ [+ ADD A SOURCE]

AMET CONSECTUTER
Cityname, State 🗑 ✏ [+ ADD A SOURCE]

[+ ADDITIONAL FACT]

[Cancel] [Save]

1051 1052
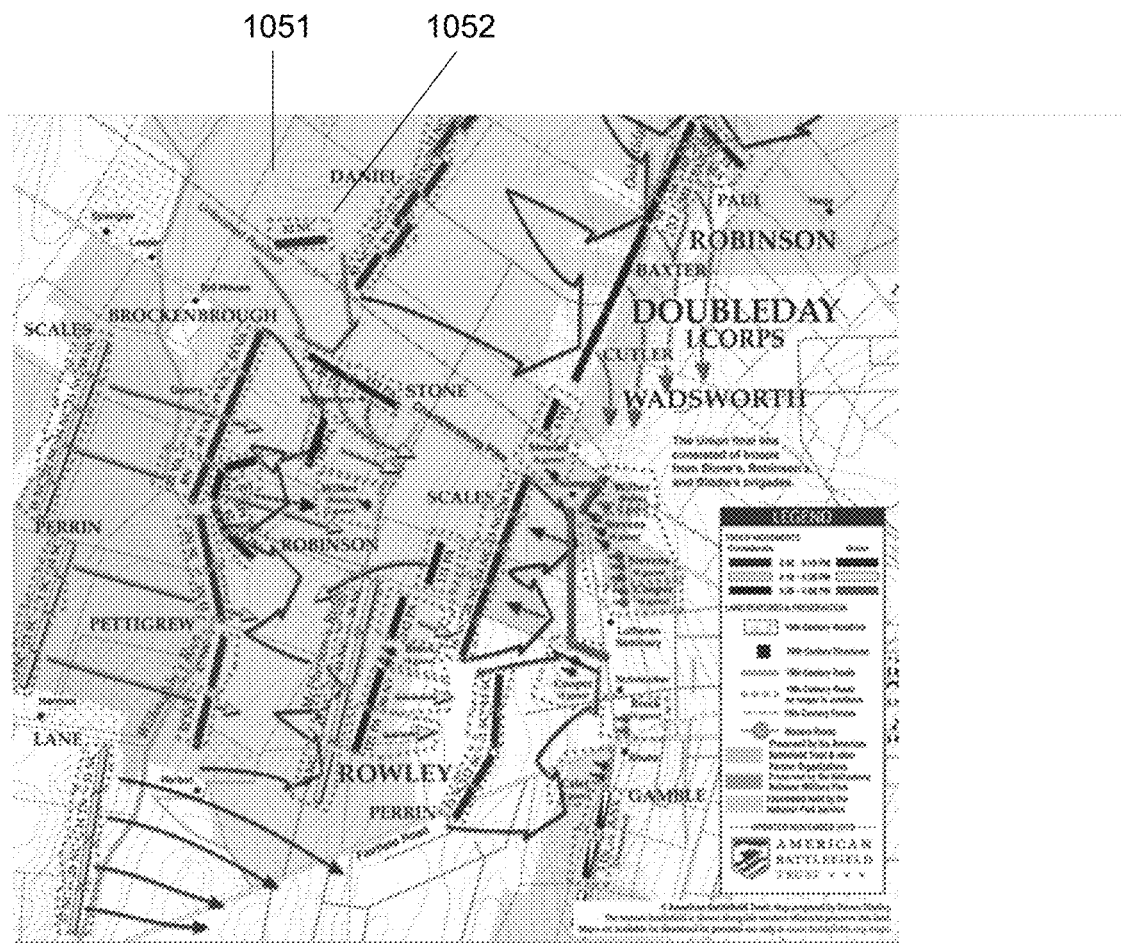
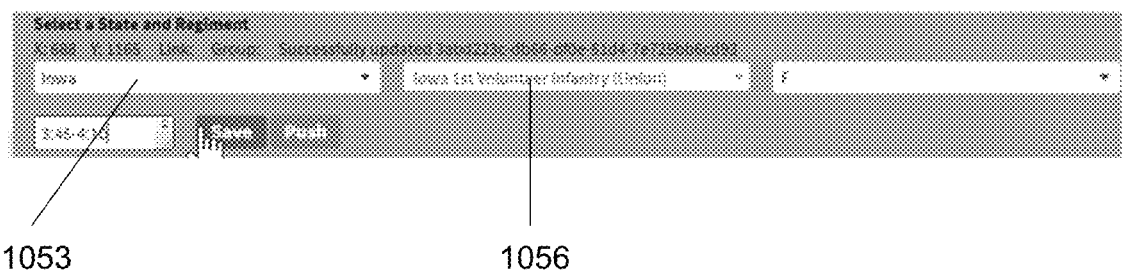
1053 1056
1050
*FIG. 10B*

DETERMINING RELATIONSHIPS OF HISTORICAL DATA RECORDS

CROSS-REFERENCE TO RELATED APPLICATION

The present application claims the benefit of U.S. Provisional Patent Application No. 63/308,659, filed on Feb. 10, 2022, which is hereby incorporated by reference in its entirety.

FIELD

The disclosed embodiments relate to determining relationships among historical data records in a large scale database.

BACKGROUND

Genealogy has been increasingly popular as people derive satisfaction from connecting with their ancestors and relatives through family trees and family-specific documents, photos, and other memorabilia. In particular, people find joy and self-actualization from understanding and connecting with their roots. Genetic genealogy services that combine DNA testing with genealogical research such as family tree building have allowed people to connect with long-lost relatives, providing these individuals with rewarding and meaningful experiences, connection, and family ties. Such connections are often generated by, e.g., identifying relationships through linked genealogical databases and DNA-based or DNA-determined ethnicities or communities. Genealogical research services, however, are generally focused on family connections and have not been suited for providing social information. For example, genealogical research services are not suited to contextualizing ancestors within specific historical organizations, neighborhoods, or any other non-family relationships.

Social networking has also become a massively popular and useful utility for connecting people along overlapping interests, needs, work, and relationships. Social networking platforms like LinkedIn allow users to connect with coworkers, collaborators, and potential business contacts while Facebook and Instagram allow users to stay in touch with distant family and friends. But existing social networking platforms, however useful, are inherently limited to relationships between living persons who must manually and actively participate in and create the interactions thereon, for example by establishing connections with each other through connection requests, friend requests, follow requests, etc., and by sending or publishing messages, posts, likes, comments, and other interactions between each other.

Despite the popularity of social networks generally and genealogical research generally, there is no existing modality that allows a person to understand historical communities, groups, and relationships. While genealogical research allows a person to connect with and to some degree vicariously experience the life events of an ancestor, for example, there is no way for a person to discern how that ancestor was influenced by or participated in a community such as a military unit, a religious congregation, a neighborhood, a profession or trade guild, mining or mill town, or other organization, or how that ancestor interacted with other members of the same. This leaves a significant gap in a person's understanding of history generally and of their ancestor's life story in particular.

SUMMARY

In some embodiments, described herein relate to a computer-implemented method, including: receiving a plurality of genealogical records, at least a subset of the plurality of genealogical records being historical records of deceased individuals; normalizing the genealogical records into normalized genealogical records, normalizing the genealogical records including converting a text string of at least one of the genealogical records into a standardized format; stitching the normalized genealogical records into a plurality of clusters, each cluster estimated to be corresponding to an individual and including one or more genealogical records associated with the individual; identifying a life-event record that is commonly associated with a subset of clusters, the life-event record indicating that a plurality of deceased individuals are connected through a non-familial relationship in a life event documented by the life-event record; and causing a graphical user interface to display a representation of a historical network among the plurality of deceased individuals that are connected through the non-familial relationship in the life event.

In some embodiments, the plurality of genealogical records includes genealogical records from a genealogical tree database, wherein stitching the normalized genealogical records includes searching for related records from the genealogical tree database.

In some embodiments, searching is performed using Elasticsearch.

In some embodiments, the method may further include: assigning a first token for each cluster in a first plurality of clusters generated in a first stitch run, the first token for each cluster representing a set of genealogical records that are identified to be stitched as the cluster in the first stitch run; assigning an identifier to each cluster in the plurality of clusters, the identifier being used by a genealogy server as the identifier of the individual corresponding to the cluster; assigning a second token for each cluster in a second plurality of clusters generated in a second stitch run, the second representing for each cluster representing a set of genealogical records that are identified to be stitched as the cluster in the second stitch run; and matching the second token with the identifier.

In some embodiments, the life-event record is a record of a military unit and the life event is joining the military unit together, and wherein the representation of the historical network indicates that the plurality of deceased individuals were in the military unit.

In some embodiments, the method may further include: organizing the normalized genealogical records based on a database schema.

In some embodiments, the database schema corresponds to a schema of a graph database.

In some embodiments, the historical network represents a historical organization, the computer-implemented method further including: generating a profile for a historical organization, the profile including information from one or more genealogical records that are stitched to the subset of clusters; and causing the graphical user interface to display the profile.

In some embodiments, the method may further include converting the text string of at least one of the genealogical records into the standardized format includes changing a name in the genealogical record to the standardized format.

In some embodiments, stitching the normalized genealogical records is based at least in part on names in the normalized genealogical records being in the standardized format.

In some embodiments, the method may further include: causing the graphical user interface to display roles of one or more deceased individuals in the non-familial relationship.

In some embodiments, the method may further include: connecting at least one of the deceased individuals in the historical network to a family tree, the family tree including one or more descendants of the deceased individual; and causing the graphical user interface to display the family tree in response to a user selecting the deceased individual in the historical network.

In some embodiments, the method may further include: determining that two users of a genealogy server are descendants of two deceased individuals in the historical network; and causing the graphical user interface to send a notification indicating the two users are connected through the historical network.

In some embodiments, a non-transitory computer-readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

BRIEF DESCRIPTION OF THE DRAWINGS

Figure (FIG. 1 illustrates a diagram of a system environment of an example computing system, in accordance with some embodiments.

FIG. 6 illustrates a user interface of a historical social network, in accordance with some embodiments.

FIG. 7 illustrates a user interface of a historical social network, in accordance with some embodiments.

FIGS. 9A, 9B, and 9C illustrate a user interface of a historical social network, in accordance with some embodiments.

FIG. 10B illustrates an administrator panel for the user interface of FIG. 8A, in accordance with some embodiments.

Figure 1:
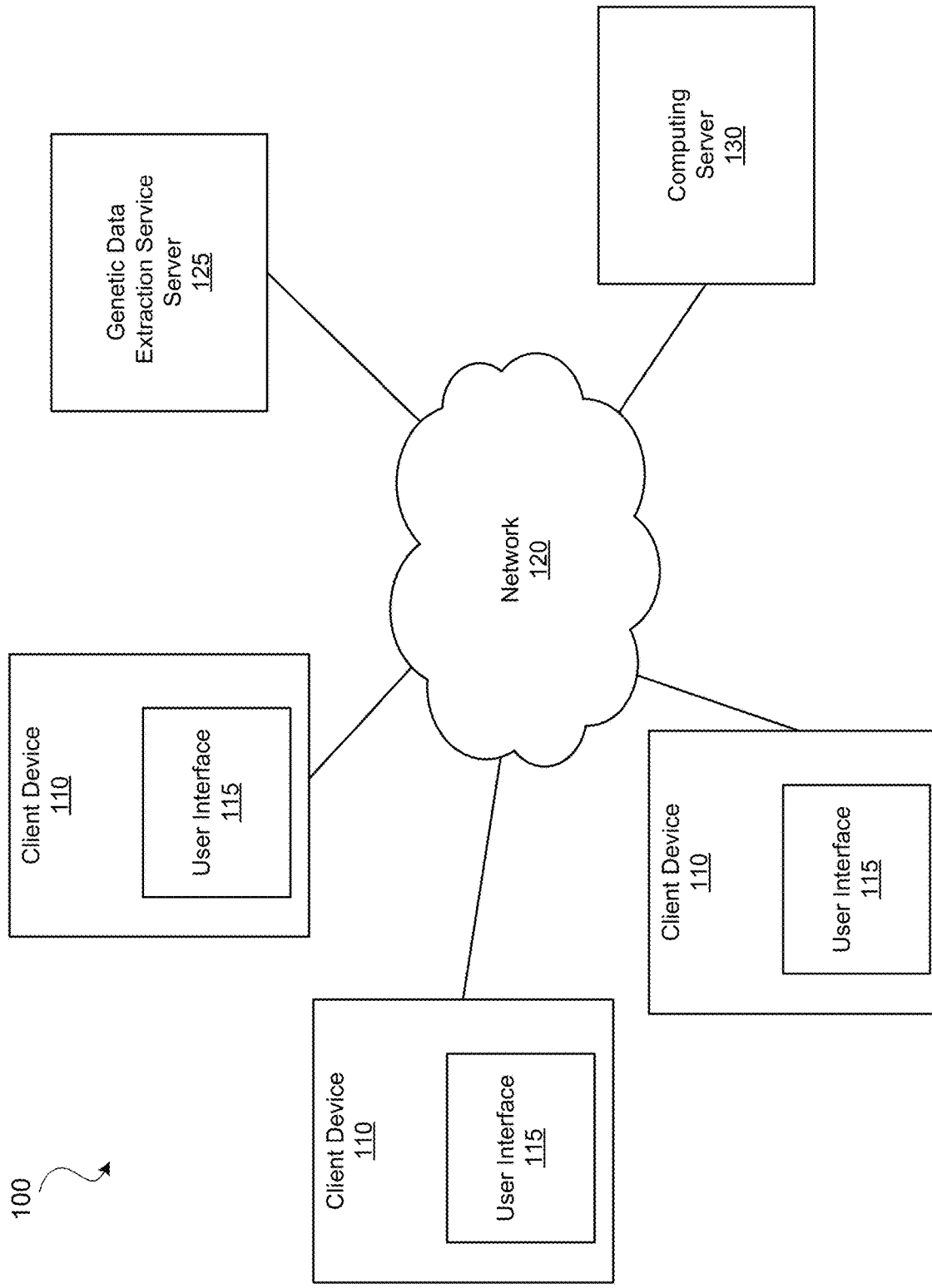

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGS.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Historical social network embodiments of the disclosure advantageously address one or more of the drawbacks in existing social networking and genealogical research approaches by facilitating automated and accurate retrieval, transformation, and presentation of information for the automatic generation of historical social networks. The automatic generation of historical social networks using embodiments of the present disclosure facilitates understanding of and connection with historical relationships, organizations, and communities such as military units, church congregations, neighborhoods, family or small church graveyards, professional organizations, mining and mill towns, and other modalities by which people were connected in the past.

Embodiments of the disclosure further generate and provide information about how such organizations and communities and members thereof participated in larger historical events, such as wars, economic phenomena, natural disasters, human migrations, technological and social revolutions, cultural events, etc. Knowledge of a person's membership in one or more such historical entities yields information about the person, including valuable context for said person's life.

In some embodiments, a historical social network is generated by retrieving, from a collection or storage, one or more records or data, normalizing the data, stitching the data, connecting the stitched data to a stitched tree database, and connecting the stitched data to contextual data. This may be performed using an search of a database, such as an ElasticSearch database, and persisted using a Neptune database, a graph database, or otherwise. Contextual data is generated by performing backend refining and utilizing one or more models for extracting facts therefrom.

Historical social network embodiments of the present disclosure advantageously facilitate automatic retrieval, normalization, and stitching of data by providing one or more models, which may be rule-based, machine learned, combinations thereof, or otherwise, to retrieve data from disparate collections, and normalize the data for a specific context. Data may be augmented as necessary by making inferences for missing fields based on other data.

Normalization approaches may advantageously address data inconsistencies and issues such as abbreviations, run-on words, multiple names, etc. For instance, the 27th unit of a particular faction or unit may also be referred to by a self-designated appellation such as the "Rock Ridge Rifles." Data specific to historical social networks for military units in the American Civil War may include, but are not limited to, muster in, muster out, imprisoned, wounded, payroll, promotions, enlisted, etc. Dates in particular can be difficult to normalize due not only to inconsistencies in how dates are written but also in inherent imperfections in the dates; that is, due to record-keepers being wrong or imprecise about the date being recorded. Location data is also a major challenge due to dynamic location-specific information. For example, West Virginia did not exist until partway through the American Civil War.

Normalization approaches according to embodiments of the disclosure may utilize a suitable Application Programming Interface ("API") to access and retrieve location information from a suitable historical place database, identify therefrom a location identification and/or time, and identify a current name for the location. The identified name may be provided to a suitable location or storage, such as a genealogical tree database, a stitched tree database, or otherwise. Similar approaches may be used to resolve inconsistent or changed names of, e.g., cemetery names, mining or mill towns, etc. Additionally, in military unit-related contexts, normalization approaches resolve the problem of inconsistent battle names by normalizing battlefield with GPS locations.

The normalized genealogical records may then be run through, for example, Amazon Elastic MapReduce ("EMR") to represent the normalized genealogical records in a data storage or database schema that is consistent or compatible with any suitable storage modality. For example, data normalized as described above may advantageously be comparable, transformable, and/or integrable into databases such as a stitched tree database, a record database, a tree database, and/or other storage modalities. The normalized genealogical records may be then be suitable for stitching or merging together with other records or data, including existing records or data. A storage modality for the normalized genealogical records may be a suitable graph database, such as an Amazon Neptune database available from Amazon.com, Inc. of Seattle, WA.

Additionally, or alternatively, the normalized genealogical records may be stitched and/or clustered to link individuals and organizations together. Such stitching and clustering methods may be based on methods described in U.S. Patent Application Publication No. 2020/0394188, published Dec. 17, 2020, and U.S. Patent Application Publication No. 2018/0189379, published Jul. 5, 2018, each of which is incorporated herein in its entirety by reference. Entity resolution techniques described in U.S. Patent Application Publication No. 2021/0319003, published Oct. 14, 2021, U.S. Patent Application Publication No. 2020/0257707, published Aug. 13, 2020, are likewise incorporated herein in their entirety by reference.

For example, stitching algorithms may be customized for the generation of historical social networks by incorporating one or more rules specific to a context and/or type of organization. In some embodiments where historical social networks are built for American Civil War military units, rules may be added to match or identify a regiment/company name, identify a state of a unit, determine a service branch, assign a faction (such as Union or Confederacy), etc. Further discretizations may include dividing into Union troops, Confederate troops, African American troops, Union sailors, Confederate sailors, or otherwise. Other rules may be relaxed, for example based on a scope or scale of a stitching operation. Rules for stitching members of a particular unit, such as a regiment, together, as compared to stitching members of a faction or from a particular state, may be comparatively relaxed.

Stitching records pertaining to organizations such as Civil War military units is not a trivial task as regiments were mostly organized by States, and each State had its own records with varying rules, conventions, and nomenclatures. There is no complete source of records, and many of the existing records have challenging redundancies, inconsistencies, and missing information. Some records available for and utilized for stitching include Civil War Soldier records, Civil War Soldier Records and Profiles records, Civil War Pension Index, Civil War Draft Registration Records, Confederate Soldiers Service Records, Civil War Prison of War records, 1890 Veterans Schedules, Union Soldiers Compiled Service records, Civil War Muster Roll Abstracts from New York, Pennsylvania Muster Rolls, Alabama Civil War Muster Rolls, New Hampshire Civil War Service and Pension Records, Indiana Civil War Soldier Database Index, Civil War Roll of Honor, Pennsylvania Veterans Burial Cards, Headstones Provided for Deceased Union Civil War Veterans records, New York Town Clerks' Registers of men who served in the Civil War, Minnesota Civil War records, Kansas Enrollment of Civil War Veterans records, U.S. Headstone Applications for Military Veterans, American Civil War General Officers records, Register of Colored Troop Deaths During Civil War records, and others.

For World War I ("WWI") stitching, different collections of records may be used. These may include Pennsylvania Veterans Card files, 1930 US Census, 1920 US Census, Social Security Death Index, 1910 US Census, 1900 US Census, Marine Corps Muster Rolls, WWI Draft Registration Cards, Department of Veterans Affairs VIRLS Death Files, US Army Transport Service Arriving and Departing Passenger Lists, Veterans' Gravesites, Veterans Administration Master Index, Headstone Applications for Military Veterans, Register of Enlistments, WWI Mothers' Pilgrimage records, Lists of Merchant Seamen Lost in WWI, and others. For World War II ("WWII") stitching, yet different collections of records may be used. These may include 1940 US Census, WWII Draft Cards, Marine Corps Muster Rolls, NavyMuster, Department of Veterans Affairs BIRLS Death File, WWII Draft Registration Cards, US Veterans Gravesites, WWII Army Enlistment Records, Select Military Registers records, Headstone Applications for Military Veterans, NavyMarineAwards records, Headstone and Internment Records for US Military Cemeteries on Foreign Soil, Rosters of WWII Dead, Iowa WWII Bonus Case Files, WWII Young American Patriots records, WWII Navy, Marine Corps, and Coast Guard Casualties records, New Mexico WWII Records, WWII Jewish Servicemen Cards, WWII Military Personnel Missing in Action or Lost at Sea records, WWII Prisoners of the Japanese, WWII Enlisted Men Cards, Alabama WWII Mmilitary Dead and Wounded records, US 1950 Census, and others.

In some embodiments, stitching is performed offline by storing the normalized genealogical records into a cache and then performing the stitching in a regression environment. It has been found that offline stitching provides flexibility to increase a number of results requested from 20 up to 100. In some embodiments, a search engine, such as an elasticsearch-based search engine, may be utilized to identify and/or determine records similar to a particular record of interest. Upon determining that an identified record is sufficiently similar to the particular record of interest, the identified record is added to a cluster, with new clusters created for new records for which an existing record and cluster is not a match.

Normally, stitching, e.g. clustering, is performed by assessing each record or node to determine whether it is satisfactory for stitching. Certain records are deemed unsatisfactory for stitching, as they do not self-compare with a sufficiently high score. Other records self-compare sufficiently well but lack a cluster to join. These may be used to create a new cluster or may be categorized as "unstitched." The criteria to create a cluster are further restrictive. To form a new cluster, a record must self-compare as "same" in multiple comparison engines and must pass a consistency check. The consistency check includes not having conflated issues, such as being born before one's mother or father. The record must also have a requisite scope in name, place, and time, which may be inferred from relatives. Further, the record must have at least one relative. These rules are used to limit the size of a stitched genealogical tree database and safeguard its reliability. However, these rules are challenging for military records, which have few if any relatives listed.

In certain some embodiments, content-qualification rules such as those described above are relaxed from existing stitch methods. As an example, the requirement that a record have a relative may be waived. The scope for name, place, and/or time may be relaxed. As another example, query by example ("QBE")-related procedures are relaxed to be forgiving of name variance, particularly within a regiment or unit. A fuzzy name module may be used. Additionally, or alternatively, other specific rules can be added to compare organization information in addition to personal or name-related information. That is, information pertaining to an organization such as a military unit may be compared between two possibly duplicate records in addition to biographical information such as name, birth place, birth year, etc. Organization-specific information may include name, state of origin, city of origin, muster-in date, muster-out date, and/or any other suitable information. Inferences may be made to determine birth year and place based on military events. Edit distance options may be optimized or tailored to a particular regiment, unit, state, faction, etc. Initials may be used for indexing and querying, which is not normally allowed in stitching.

It has been surprisingly found that organization-specific, such as military unit-specific, searching is finite enough to allow for further relaxation of rules. For instance, a regiment in the American Civil War could contain approximately 1,000 individuals, between whom the likelihood of overlapping names is reduced compared to a standard clustering situation. This facilitates relaxation of name-specific rules. Further, in elasticsearch, typically initials are not indexed because of cost, but in some embodiments initials are indexed.

While name-specific rules may be relaxed within a regiment, to prevent overstitching, other rules may be utilized. For example, even if the name and regiment data match for two records, comparisons may be drawn between, e.g., enlistment city, county, and state, enlistment year, enlistment date, one record had events after the death of the other, birth years off by four or more years, different company names when enlisted, one survived the war but the other did not, combinations and/or alterations thereof, or any other suitable rule.

Existing schemas for holding details about entities, such as individuals, in a tree database, cluster database, and/or stitched tree database, may include important details such as name, birth place, birth date, etc., but existing schemas lack information needed for linking individuals to organizations. Database schemas may be updated for records or data input for and corresponding to historical social networks and/or for existing data and records.

A database, for example a graph database such as a Neptune database, may be used to store data about individuals and organizations, with individuals being represented as nodes and relationships therebetween being represented as edges. For example, a stitched tree database, genealogical tree database, or otherwise may be a graph database. The database may likewise comprise data regarding contextual information obtained through or generated by performing backend refining and utilizing one or more models for extracting pertinent facts from contextual information.

The data thus transformed and stitched together in the database may be presented to a user as a historical social network, with automatically determined or generated profiles or pages for particular organizations (such as military units, e.g. a regiment and its subsidiary companies) and individual members thereof. The profiles or pages of organizations and/or individuals may be automatically populated with contextual facts, e.g. data pertaining to events relevant to the organizations and/or individuals. A regiment profile for an American Civil War unit, therefore, may present extracted facts pertaining to particular battles in which the regiment participated (as determined by the normalized genealogical records for the regiment) and a link to profiles for individuals who participated therein.

The transformed and stitched-together data in or associated with a historical social network may, in some embodiments, be used for or integrated with a genealogical research service. Whereas many users of a genealogical research service may only have birth, marriage, and death information about an ancestor to use for searching for relevant records, many military records do not have any birth, marriage, and death information. It has been found that clusters developed or generated using embodiments of the disclosure for historical social networks may be integrated with existing clusters in a stitched genealogical tree database for searching- and/or hints-related purposes.

This may include determining that military record that has been found by a customer as part of a search is part of a military cluster, and then serving up other members of the cluster as additional suggestions/hints. If a regiment cluster member is also stitched as a member of a cluster in the stitched genealogical tree database and a member tree person "connects in" to that cluster, the remaining members can be served up as hints for the target person. If a member tree person "connects in" to a cluster that has another member tree person that has attached one or more military cluster members, the attached and other cluster members can be served up as hints. All military clusters one by one may be fed into an exhaustive and/or fuzzy query to find existing stitched genealogical tree database clusters that match them. A cluster representative or aggregate placeholder person can be stitched into the cluster and treated as a primary connection.

Example System Environment

FIG. 1 illustrates a diagram of a system environment 100 of an example computing server 130, in accordance with some embodiments. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliances (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In some embodiments, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In some embodiments, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In some embodiments, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In some embodiments, a set of SNPs (e.g., 300,000) that are shared between different array platforms (e.g., Illumina OmniExpress Platform and Illumina HumanHap 650Y Platform) may be obtained as genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in some embodiments, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In some embodiments, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, and phenotypes are examples of biomarkers.

The computing server 130 performs various analyses of the genetic data, genealogy data, and users' survey responses to generate results regarding the phenotypes and genealogy of users of computing server 130. Depending on the embodiments, the computing server 130 may also be referred to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In some embodiments, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In some embodiments, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
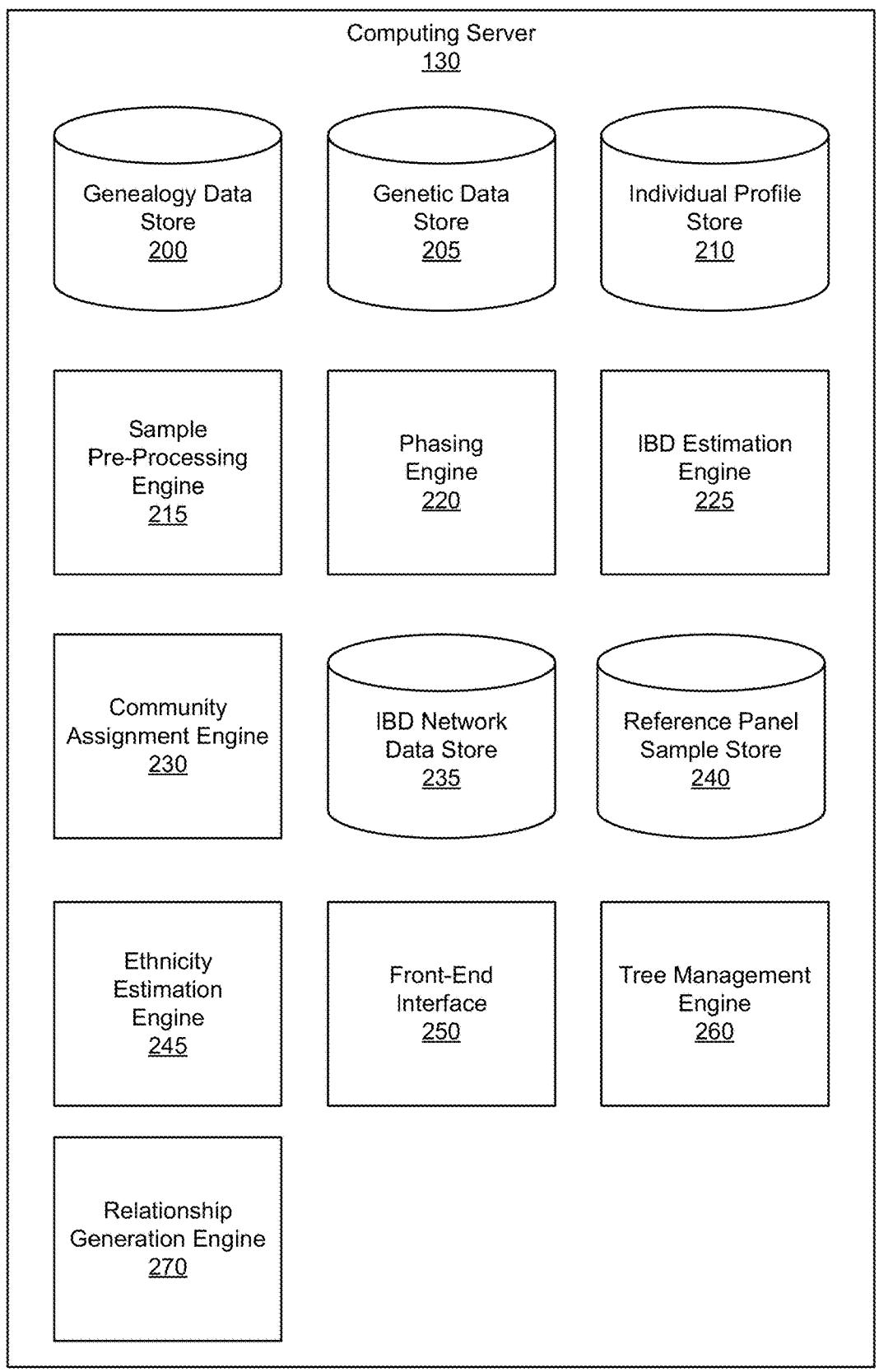
FIG. 2 is a block diagram of an architecture of an example computing system, in accordance with some embodiments.

FIG. 2 is a block diagram of an architecture of an example computing server 130, in accordance with some embodiments. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, a front-end interface 250, a tree management engine 260, and a relationship generation engine 270. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among users of the computing server 130. The information related to the connections among a user and her relatives that may be associated with a family tree may also be referred to as pedigree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data on the whole or portions of an individual's genome. The genetic data store 205 may store a pointer to a location associated with the genealogy data store 200 associated with the individual. A genetic dataset may take different forms. In some embodiments, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to a SNP site. A SNP locus may be associated with a unique identifier. The genetic dataset may be in a form of diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may be a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 205. The metadata about the individual may also be individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In some embodiments, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 130 may obtain data on a user's disease-related phenotypes from survey questions about the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video game preferences, etc. Other questions may be related to the users' diet preferences such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may be subject to the privacy and authorization setting of the users to specify any data related to the users that can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access to the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and researches conducted by the computing server 130 such as a large-scale genetic study. On yet another level, the user may turn some portions of her genealogy data public to allow the user to be discovered by other users (e.g., potential relatives) and be connected to one or more family trees. Access or sharing of any information or data in the computing server 130 may also be subject to one or more similar privacy policies. A user's data and content objects in the computing server 130 may also be associated with different levels of restriction. The computing server 130 may also provide various notification features to inform and remind users of their privacy and access settings. For example, when privacy settings for a data entry allow a particular user or other entities to access the data, the data may be described as being "visible," "public," or other suitable labels, contrary to a "private" label.

In some cases, the computing server 130 may have a heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in to sharing of those data or change the default privacy settings. In other cases, the heightened privacy settings may apply across the board for all data of certain groups of users. For example, if computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125.

The sample pre-processing engine 215 identifies autosomal SNPs in an individual's genetic dataset. In some embodiments, the SNPs may be autosomal SNPs. In some embodiments, 700,000 SNPs may be identified in an individual's data and may be stored in genetic data store 205. Alternatively, in some embodiments, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No. 10,679,729, entitled "Haplotype Phasing Models," granted on Jun. 9, 2020, describes example embodiments of haplotype phasing. Other example phasing embodiments are described in U.S. Patent Application Publication No. US 2021/0034647, entitled "Clustering of Matched Segments to Determine Linkage of Dataset in a Database," published on Feb. 4, 2021.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720,229, entitled "Reducing Error in Predicted Genetic Relationships," granted on Jul. 21, 2020, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of the times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, and other quality control. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In some embodiments, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2020 and U.S. Pat. No. 10,692,587, granted on Jun. 23, 2020, entitled "Global Ancestry Determination System" describe different example embodiments of ethnicity estimation.

The front-end interface 250 displays various results determined by the computing server 130. The results and data may include the IBD affinity between a user and another individual, the community assignment of the user, the ethnicity estimation of the user, phenotype prediction and evaluation, genealogy data search, family tree and pedigree, relative profile and other information. The front-end interface 250 may allow users to manage their profile and data trees (e.g., family trees). The users may view various public family trees stored in the computing server 130 and search for individuals and their genealogy data via the front-end interface 250. The computing server 130 may suggest or allow the user to manually review and select potentially related individuals (e.g., relatives, ancestors, close family members) to add to the user's data tree. The front-end interface 250 may be a graphical user interface (GUI) that displays various information and graphical elements. The front-end interface 250 may take different forms. In one case, the front-end interface 250 may be a software application that can be displayed on an electronic device such as a computer or a smartphone. The software application may be developed by the entity controlling the computing server 130 and be downloaded and installed on the client device 110. In another case, the front-end interface 250 may take the form of a webpage interface of the computing server 130 that allows users to access their family tree and genetic analysis results through web browsers. In yet another case, the front-end interface 250 may provide an application program interface (API).

The tree management engine 260 performs computations and other processes related to users' management of their data trees such as family trees. The tree management engine 260 may allow a user to build a data tree from scratch or to link the user to existing data trees. In some embodiments, the tree management engine 260 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In some embodiments of automatic tree matching, the tree management engine 260 may receive a genetic dataset from the target individual as input and search related individuals that are IBD-related to the target individual. The tree management engine 260 may identify common ancestors. Each common ancestor may be common to the target individual and one of the related individuals. The tree management engine 260 may in turn output potential family trees to which the target individual may belong by retrieving family trees that include a common ancestor and an individual who is IBD-related to the target individual. The tree management engine 260 may further identify one or more probable positions in one of the potential family trees based on information associated with matched genetic data between the target individual and those in the potential family trees through one or more machine learning models or other heuristic algorithms. For example, the tree management engine 260 may try putting the target individual in various possible locations in the family tree and determine the highest probability position(s) based on the genetic dataset of the target individual and genetic datasets available for others in the family tree and based on genealogy data available to the tree management engine 260. The tree management engine 260 may provide one or more family trees from which the target individual may select. For a suggested family tree, the tree management engine 260 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 260 may automatically search, rank, and suggest individuals for the user conduct manual reviews as the user makes progress in the front-end interface 250 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

The relationship generation engine 270 determines relationships among data records to identify a cluster for records that belong to the same individual. The relationship generation engine 270 may apply one or more pipelines to generate a historical network that describes the relationships. Details of the operation of the 270 is further discussed below in FIG. 3 and FIG. 4.

Example Historical Network Generation Pipeline

Figure 3:
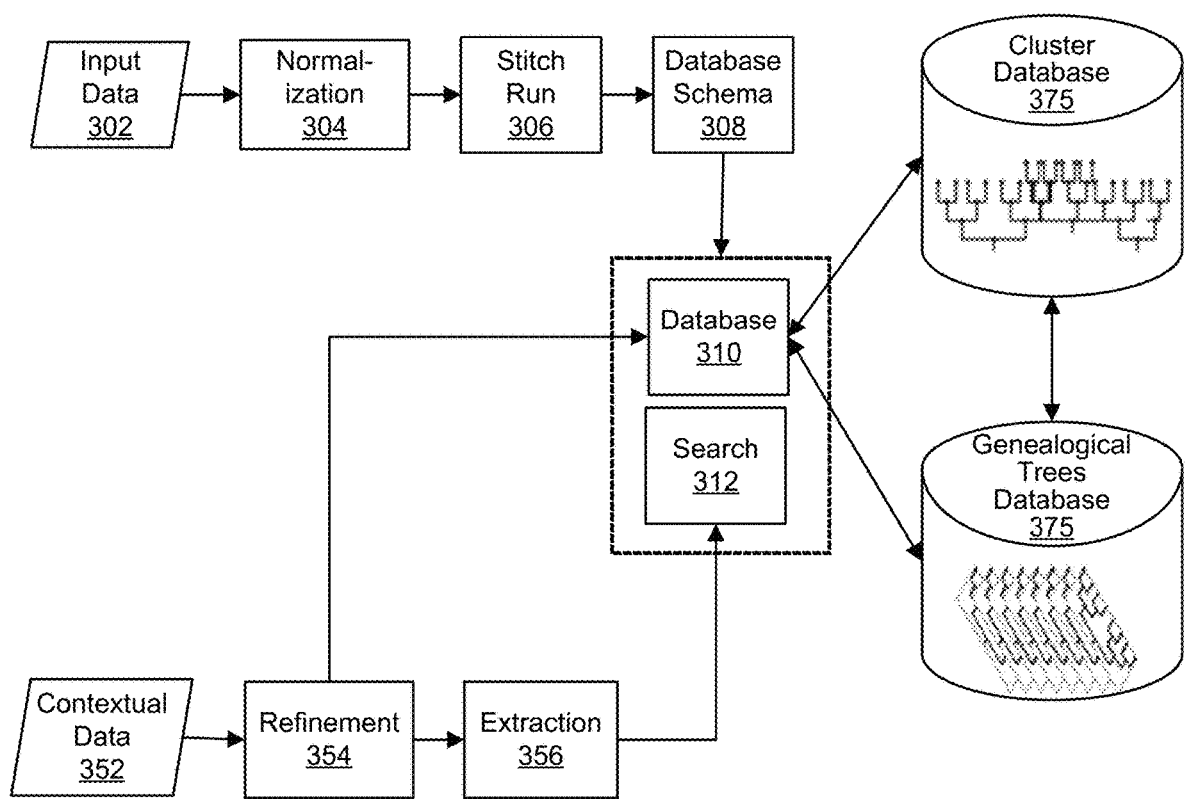
FIG. 3 is a block diagram illustrating a pipeline for generating a historical social network, in accordance with some embodiments.

FIG. 3 is a block diagram illustrating a pipeline for generating a historical social network, in accordance with some embodiments. One or more steps in the pipeline 300 may be performed by the relationship generation engine 270 in connection with other components of the computing server 130.

Embodiments of historical social network systems and methods according to the present disclosure address shortcomings in the art by facilitating automated and accurate retrieval, transformation, storage, linking, and presentation of information for the automatic generation of historical social networks. The automatic generation of historical social networks using embodiments of the present disclosure facilitates understanding of and connection with historical relationships, organizations, and communities such as military units, church congregations, neighborhoods, family or small church graveyards, professional organizations, mining and mill towns, and other modalities by which people were connected in the past. The historical social networks of embodiments further provide contextual information from historical phenomena and transform, store, and present such information along with the determined historical relationships.

In some embodiments, historical social networks and systems, methods, and computer-program products further generate and provide information about how such organizations and communities and members thereof participated in larger historical events, such as wars, economic phenomena, natural disasters, human migrations, technological and social revolutions, etc. Knowledge of a person's membership in one or more such historical entities yields information about the person, including valuable context for said person's life. Historical social networks of embodiments further detail how a person participated in such historical entities and phenomena and with whom the person associated.

In some embodiments, a historical social network is generated by retrieving, from a collection or storage, one or more records or data, such as historical records, normalizing the data, stitching the data, connecting the stitched data to a stitched genealogical tree database, and connecting the stitched data to contextual data. This may be performed using a search of a database, such as an ElasticSearch database, and persisted using a Neptune database, a graph database, or otherwise. Contextual data is generated by performing backend refining and utilizing one or more models for extracting facts therefrom.

Historical social network embodiments of the present disclosure advantageously facilitate automatic retrieval, normalization, and stitching of data by providing one or more models, which may be rule-based, machine learning, combinations thereof, or otherwise, to retrieve data from disparate collections of records, and transform the data, for example by performing one or more normalization operations, for a specific context. Data may be augmented as necessary by making inferences for missing fields based on other data.

The pipeline 300 may include input data 302 in the form of a collection of genealogical records. Part of the collection may be historical records pertaining to a particular historical organization or phenomenon, such as a military regiment. The input data 302 may be normalized in step 304. Normalization advantageously reduces discrepancies due to, e.g., different styles or conventions of abbreviation, naming, historical locations, date recording, etc. Normalization may use rule-based, machine-learning, and/or other suitable approaches. Normalization may include the use of optical character recognition ("OCR"), handwriting recognition modalities, image segmentation, object detection, other computer vision modalities, combinations thereof, or otherwise.

In a stitch run 306, the normalized genealogical records are stitched or clustered together. The stitching or clustering may be performed using historical organization-specific algorithms for entity resolution and clustering, for example, historical organization-specific clustering algorithms wherein rules for names, including name variance, are relaxed. This allows the stitch run 306 to search the normalized genealogical records for similar records. For example, the computing server 130 may determine whether records in the normalized genealogical records are similar to a particular record of interest, and cluster certain similar records together. Searching the normalized genealogical records may be performed using a search engine such as Amazon Elasticsearch or any other suitable search modality. Searching may be performed offline by putting certain of the normalized genealogical records in an offline cache and stitching the records in a regression environment.

The computing server 130 may determine a database schema 308 for the normalized and stitched data. According to the database schema 308, the computing server 130 may arrange the normalized and stitched data in, e.g., a relational scheme and/or as a JSON data transfer format for describing people and data associated therewith, for example, names, gender, locations, affiliations, etc. Support for genealogical tree information is likewise supported in some embodiments. For example, evidence such as citations and sources of information, such as attached records or corresponding genealogical tree nodes, may be included. In other embodiments, the database schema 308 may be in an XML format configured to represent people and associated attributes and relationships.

In some embodiments, while a stitch run 306 is shown upstream of determining a database schema 308, stitching is not performed until after the normalized genealogical records are arranged in the database schema 308. By organizing and transforming the normalized genealogical records into the database schema, the data can advantageously be stitched and/or clustered together for efficient and automated entity resolution and for drawing connections between individuals. For example, a person may be identified from a historical record, such as a Civil War regiment enlistment record. Other data, such as the person's participation in certain events or battles of interest as part of the Civil War regiment, may be included in the database schema for the node presenting that person.

The genealogical records, upon being stitched together as clusters with each cluster representing a person albeit from a different record entirely (such as a birth, marriage, death, or Census record), allow a user to review both the information contained in the birth, marriage, death, or Census record along with the Civil War regiment information. This facilitates a more holistic and complete view of the person than would be possible relying on the sources independently of each other, and clustering thereof is made possible only by the provision of a system, method, and/or computer-program product for historical social networks according to embodiments, as the normalized genealogical records from historical records is able to be combined with data from other records, yielding combined insights and context that would have been unavailable with one set of data alone.

The normalized genealogical records may be stored, stitched, and/or transformed in a database 310, such as a graph database. The database 310 may be part of the genealogy data store 200. The database 310 may include or be configured to cooperate with a cluster database 375 and/or a genealogical trees database 376. This advantageously allows for stitching the normalized genealogical records together with other records, such as those associated with genealogical trees on a genealogical research service platform. Such genealogical trees may be clustered together to perform entity resolution and provide other insights in the cluster database 375. A search 312, such as an Elasticsearch modality, may be utilized to search for relevant records or persons relative to a particular record or individual of interest. One or more of the database 310, the cluster database 375, and the genealogical trees database 376 may be transformed by the stitching operation. For example, the normalized genealogical records may be added to relevant clusters of the cluster database 375, pertinent nodes of the genealogical trees database 376 may be populated with pertinent data from the normalized genealogical records, and so on.

Alternatively, or additionally, previously, subsequently, or in parallel, contextual data 352 may be received and passed to backend refinement 354. This may likewise normalize the contextual data. The refined data may be passed directly to the database 310 and/or to an extraction engine 356 that extracts pertinent data from the refined data. Extraction 356 may instruct one or more algorithms for determining the pertinence of data. The algorithms for extracting contextual information may include algorithms for extracting or surmising details about a particular historical organization.

Such algorithms or rules may include, in some embodiments, algorithms for determining facts about members of the organization, such as the total number of soldiers, date of joining the organization, the most common place of joining the organization, most common date of joining the organization, the most common residence of members, the name of youngest and/or oldest members of the organization, average age of the members of the organization, number of members of the organization who experienced a pertinent event (such as injury, death, or otherwise), etc. In some embodiments directed to military units in a conflict, for example, facts about a particular regiment may be surmised, extracted, compiled, or otherwise transformed from records to determine the number of individuals therein who died or were injured in a particular conflict or battle.

Sources of contextual information, such as Wikipedia.org, may be automatically scraped using algorithms or scripts for obtaining and transforming information regarding events of, e.g., a historical conflict like the American Civil War. The historical social network embodiments directed in particular to conflicts such as the American Civil War may be configured to automatically search for, identify, extract from, and transform data from pages on Wikipedia.org, American Battlefield Trust, and other sources. For a particular organization, such as the North Carolina $20^{th}$ Infantry Company, any known names or abbreviations for the organization may be utilized during the search and identification process and/or during the transformation process. As a result, instances where the North Carolina $20^{th}$ Infantry Company is listed as a participant in a particular page describing a particular battle, e.g., the battle of Gaines' Mill or Chancellorsville, are retrieved and transformed such that these battles are listable on and linked within a page or profile for the North Caroline $20^{th}$ Infantry Company. This process may be automatically carried out for each company, regiment, etc. of a desired conflict.

The scraping process may include automatically identifying state pages that include lists of state-based or -originated units in a particular conflict. For example, a page listing unit from Pennsylvania in the American Civil War may be used to identify and obtain links for each unit, and then each identified unit-specific page may be scraped to retrieve desired details.

Historical Network Identification Process

Figure 4:
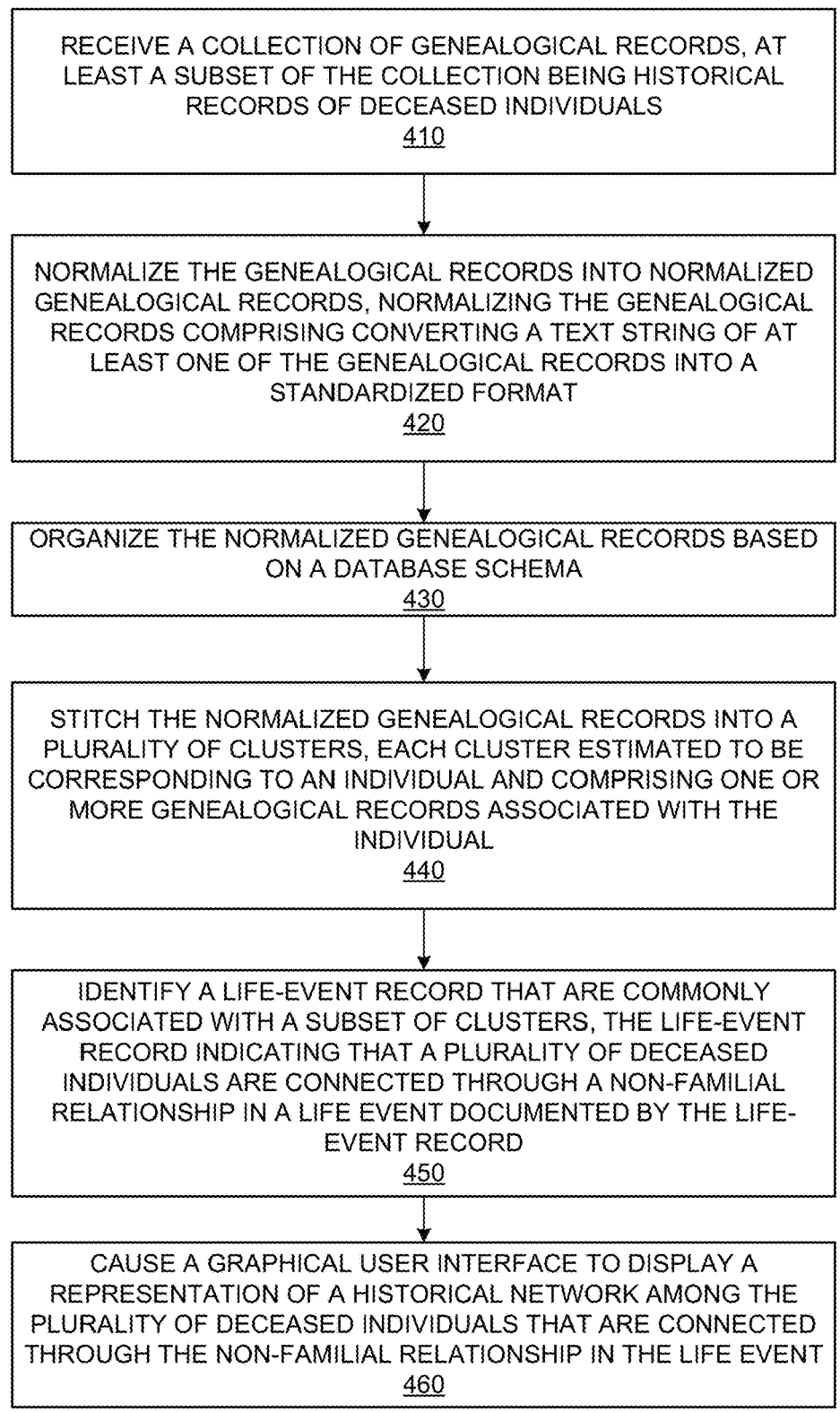
FIG. 4 is a flowchart depicting an example process for identifying and displaying a historical network, in accordance with some embodiments.
Figure 5:
FIG. 5 illustrates a user interface of a historical social network, in accordance with some embodiments.

FIG. 4 is a flowchart depicting an example process 400 for identifying and displaying a historical network, in accordance with some embodiments. The process may be performed by one or more engines of the computing server 130 illustrated in FIG. 2, such as the relationship generation engine 270. The process 400 may be embodied as a software algorithm that may be stored as computer instructions that are executable by one or more processors. The instructions, when executed by the processors, cause the processors to perform various steps in the process 400. In various embodiments, the process may include additional, fewer, or different steps. While various steps in process 400 may be discussed with the use of computing server 130, each step may be performed by a different computing device.

In some embodiments, process 400 can include receiving a plurality of genealogical records (step 410). The plurality of genealogical records do not need to be from the same datasets. For example, the genealogical records can include various genealogical collections, as described in the examples provided in the genealogy data store 200, such as historical records (e.g., records related to an ancestor), medical records, military records, photographs, other records indicating one or more traits, and other suitable recorded data. In some embodiments, some of the genealogical records are historical records of deceased individuals. In some embodiments, some of the genealogical records may include historical records that are digitalized from physical records. In some embodiments, some of the genealogical records may be retrieved from the cluster database 375 and/or the genealogical trees database 376.

The record data may be received or retrieved from a record collection, a database, or any other suitable location or storage modality. The record data may include digitized images of historical records such as Census or other documents, database data, or any other suitable source of information. The record data may pertain in particular to historical organizations or entities such as neighborhoods, military units, mining or mill towns, trade guilds, etc.

Continuing with reference to FIG. 4, in some embodiments, process 400 can include normalizing the genealogical records into normalized genealogical records (step 420). Normalizing the genealogical records may include various steps and pipelines to improve and standardize the records. For example, normalizing the genealogical records may include converting a text string of at least one of the genealogical records into a standardized format, assigning a named entity with different names to the same identifier, fixing typographical errors, mapping historical concepts with different names to the same concept, and additional data preprocessing steps.

The normalization of records may also include applying one or more transformations to the data from different collections, sources, etc. to ensure consistent treatment and representation of the data. Such transformations may be performed by or using rule-based, machine learning, or other approaches, and may pertain to dates, names, abbreviations, run-on words, locations, etc. Normalization transformations may be performed utilizing a rule-based approach, for example by normalizing battlefield locations with global positioning system ("GPS") locations and/or historical location databases.

Normalization approaches may advantageously address data inconsistencies and issues such as abbreviations, run-on words, multiple names, etc. that hinder manual and automated attempts to collate, transform, or otherwise discern information from such data. For instance, the $27^{th}$ unit of a particular faction or military unit may also and inconsistently be referred to by a self-designated appellation such as the "Rock Ridge Rifles." Data specific to historical social networks for military units in the American Civil War may include, but are not limited to, muster in date, location, and other information, muster-out date, location, and other information, imprisoned, wounded, payroll, promotions, enlisted, etc.

Dates in particular can be difficult to normalize not only due to inconsistencies in how dates are written in certain records, but also due to inherent imperfections in the dates; that is, due to record-keepers being wrong or imprecise about the date being recorded. Location data is also a major challenge due to dynamic location-specific information. For example, West Virginia did not exist until partway through the American Civil War. Thus, a location may have been recorded as being in Virginia which, according to modern maps, would actually say West Virginia today. Similar effects can occur in cities, towns, counties, and states that separate, merge, or otherwise change names or borders.

In some embodiments, normalization approaches may utilize a suitable Application Programming Interface ("API") to access and retrieve location information from a suitable historical place database, identify therefrom a location identification and/or time, and identify a current name for the location. The identified name may be provided to a suitable location or storage, such as a genealogical tree database, a stitched tree database, or otherwise. Similar approaches may be used to resolve inconsistent or changed names of, e.g., cemetery names, mining or mill towns, etc. Additionally, or alternatively, in military unit-related contexts, normalization approaches resolve the problem of inconsistent battle names by normalizing battlefields with GPS locations.

In some embodiments, the normalized genealogical records may then be run through, for example, a modality such as AMAZON Elastic MapReduce ("EMR") available from AMAZON.COM, Inc. of Seattle, WA, and customized appropriately, to represent the normalized genealogical records in a data storage or database schema that is consistent or compatible with any suitable storage modality. EMR may be customized in some embodiments with a task-specific program or other modality configured for stitching, entity resolution, and/or other tasks as described herein.

For example, data normalized as described above may advantageously be comparable, transformable, and/or integrable into databases such as a stitched tree database, a record database, a tree database, and/or other storage modalities. The normalized genealogical records may then be suitable for stitching, merging, or clustering together with other records or data, including existing records or data. A data store for the normalized genealogical records may be a suitable graph database, such as an AMAZON Neptune database available from AMAZON.COM, Inc. of Seattle, WA. While a graph database is described, it will be appreciated that any suitable storage modality may alternatively be utilized, such as a relational database.

Continuing with reference to FIG. 4, in some embodiments, process 400 can include organizing the normalized genealogical records based on a database schema (step 430). Existing schemas for holding details about entities, such as individuals, in a tree database, cluster database, and/or stitched tree database, may include important details such as name, birth place, birth date, etc., but existing schemas lack the information needed for linking individuals to organizations. Database schemas may be updated for records or data input for and corresponding to historical social networks and/or for existing data and records. The database schema may be a relational scheme and/or a JSON data transfer format for describing people and data associated therewith, for example, names, gender, locations, affiliations, etc. Other suitable schemas may be utilized.

A database, for example, a graph database such as a Neptune database, may be used to store data about individuals and organizations, with individuals being represented as nodes and relationships therebetween being represented as edges. For example, a stitched tree database, a genealogical tree database, or otherwise may be a graph database. The database may likewise comprise data regarding contextual information obtained through or generated by performing backend refining and utilizing one or more models for extracting pertinent facts from contextual information.

Continuing with reference to FIG. 4, in some embodiments, process 400 can include stitching the normalized genealogical records into a plurality of clusters (step 440). The normalized genealogical records may be link individuals and organizations together. Stitching may be performed using a search modality, e.g. Elasticsearch, or any other suitable search modality, to search for records or data similar to a particular record of interest. The record of interest may be a newly transformed datum or record. Stitching algorithms, which may be rule-based and/or machine learning, may compare records and data on an organizational level and/or determine membership in or affiliation with an organization, and/or may utilize organization-specific rules. Clustering—determining that two records likely pertain to the same person or entity—may be performed for records having a similarity above a threshold similarity.

Such stitching methods may be based on methods described in U.S. Patent Application Publication No. 2020/0394188, published Dec. 17, 2020, and U.S. Patent Application Publication No. 2018/0189379, published Jul. 5, 2018, each of which is incorporated herein in its entirety by reference. Entity resolution techniques described in U.S. Patent Application Publication No. 2021/0319003, published Oct. 14, 2021, U.S. Patent Application Publication No. 2020/0257707, published Aug. 13, 2020, are likewise incorporated herein in their entirety by reference and may likewise be utilized.

Stitching may be used to automatically link an individual record with another record in a collection and/or with another record in an existing repository such as a stitched tree database, wherein nodes (representing tree persons) are connected to other nodes via edges specifying specific relationships and where duplicate nodes and associated relationships are clustered together. Stitching may utilize automated measures for entity resolution and clustering, allowing one record to provide a contextual link to other records or data. Given the volume of data and records in existence, the stitching of such data and records together is a non-trivial task requiring specialized computing systems and components.

For example, stitching algorithms may be customized for the generation of one or more historical social networks by incorporating one or more rules specific to a context and/or type of organization. In some embodiments where historical social networks are built for American Civil War units and participants thereof, rules may be added to match a state of a unit, assign a faction (such as Union or Confederacy), etc. Other rules may be relaxed, for example, based on a scope or scale of a stitching operation. Stitching members of a particular unit such as a regiment together, as compared to stitching members of a faction or from a particular state, may be comparatively relaxed.

In some embodiments, stitching is performed offline by storing the normalized genealogical records in a cache and then performing the stitching in a regression environment. It has been found that offline stitching provides flexibility to increase the number of results requested from 20 to 100. In some embodiments, a search engine, such as an elasticsearch-based search engine, may be utilized to identify and/or determine records similar to a particular record of interest. Upon determining that an identified record is sufficiently similar to the particular record of interest, the identified record is added to a cluster, with new clusters created for new records for which an existing record and cluster are not a match.

In some embodiments, content-qualification rules are relaxed from existing stitch methods. For example, query by example ("QBE")-related procedures for information retrieval are relaxed to be forgiving of name variance. A fuzzy name module may be used. Additionally, or alternatively, other specific rules can be added to compare organizational information in addition to personal or name-related information. Information pertaining to an organization such as a military unit may be compared between two possibly duplicate records in addition to biographical information such as name, birth place, birth year, etc. Organization-specific information may include name, state of origin, city of origin, muster-in date, muster-out date, and/or any other suitable information.

It has been surprisingly found that organization-specific, such as military unit-specific, searching is finite enough to allow for further relaxation of rules. For instance, a regiment in the American Civil War could contain approximately 1,000 individuals, between whom the likelihood of overlapping names is reduced compared to a standard clustering situation. This facilitates the relaxation of name-specific rules. Further, in elasticsearch, typically initials are not indexed because of cost, but in some embodiments, initials are indexed. This advantageously allows for searching on initials so as to find records that do not have a full given name, e.g., "T. C. Smith."

The process of stitching or otherwise joining the data in two dimensions—one dimension being non-familial, such as regiment, and another dimension being familial such as spouse and children—allows descendants to discover contextual information about their ancestor(s) as well as to be able to connect with descendants of other involved in the event or historical group. One of the two dimensions may be a horizontal dimension that reveals or facilitates connections between contemporaries and/or non-relatives, such as a person's associates at work, in the military, in their neighborhood, or otherwise. This is in contrast to the focus of genealogical research on vertical dimensions of connection, such as between children and parents.

The historical social network embodiments thus advantageously allow for connection between individuals who, though in many cases not connected by direct-line family ties, have a significant nexus through a historical organization. The connections facilitated between the great-great-grandchildren of individuals who fought together in the Battle of Gettysburg or between the grandchildren of individuals who fought together in the Battle of the Bulge are profoundly rewarding, and can lead to connections, insights, and discovery that are not possible through direct-line family ties alone. Further, this has been found to increase interest in, and feelings of personal connection to, the events themselves.

For instance, a user who discovers that their grandfather fought in the $442^{nd}$ Regimental Combat Team (comprising almost exclusively Japanese American soldiers, many of whom were recruited from internment camps), and is privy to contextual information thereabout through the historical social network embodiment, is more likely to investigate and engage with information and resources pertaining to "the 442," to seek out information or connection with others whose ancestors were similarly involved, and to share this information. This results in connection, sharing of insights and information, and rewarding engagement that is not possible even through direct-line ancestor genealogy research.

The data thus transformed and stitched together in the database may be presented to a user as a historical social network, with automatically determined or generated profiles or pages for particular organizations (such as military units, e.g., a regiment and its subsidiary companies) and individual members thereof. The profiles or pages of organizations and/or individuals may be automatically populated with contextual facts, e.g., data pertaining to events relevant to the organizations and/or individuals. A regiment profile for an American Civil War unit, therefore, may present extracted facts pertaining to particular battles in which the regiment participated (as determined by the normalized genealogical records for the regiment) and a link to profiles for individuals who participated therein.

In some embodiments, each cluster is estimated to be corresponding to an individual and comprising one or more genealogical records associated with the individual. However, as new genealogical records are added to the genealogy data store 200 of the computing server 130, a subsequent stitch run may discover a new cluster with a different set of genealogical records, a genealogical record being stitched differently than a previous run, and a cluster in fact containing records of two individuals. The relationship generation engine 270 may execute an algorithm that matches the clusters in a stitch run to unique identifiers that may be used to identify individuals, historical or present, stored in the individual profile store 210.

For example, comparing two stitch runs that may generally be referred to as the first stitch run and the second stitch run, the relationship generation engine 270 may assign a first token for each cluster in a first plurality of clusters generated in the first stitch run. The first token for each cluster represents a set of genealogical records that are identified to be stitched as the cluster in the first stitch run. The token may be generated based on the set of genealogical records. For example, the token may be a hash of the set of genealogical records.

The relationship generation engine 270 may also assign an identifier to each cluster in the plurality of clusters. The identifier may be a unique identifier and may be different from the token. The identifier is used by the computing server 130 as the identifier of the individual corresponding to the cluster. Since each individual is assigned a unique identifier, users of the computing server 130 may provide additional data, such as user-generated content, to the individual and associate those data with the individual. The added data by the users may be propagated to the genealogical records.

As additional genealogical records are received, the relationship generation engine 270 may execute a second stitch run. The relationship generation engine 270 may assign a second token for each cluster in a second plurality of clusters generated in the second stitch run. The second represents each cluster representing a set of genealogical records that are identified to be stitched as the cluster in the second stitch run. The token may be stitch-run specific. For example, even if, in both stitch runs, there exist the same sets of genealogical records, each set will be assigned a different token. The relationship generation engine 270 in turn matches the second token with the identifier that represents the individual. For example, the relationship generation engine 270 may examine the genealogical records in each set to determine whether a cluster generated in the second stitch run is the same as another cluster generated in the first stitch. In some cases, the relationship generation engine 270 may determine that a cluster in the first run now corresponds to two clusters in the second run. In such a case, the relationship generation engine 270 may assign one of the tokens in the second run to the existing identifier and generate a new identifier for the other token. In another case, the relationship generation engine 270 may determine that two tokens in the first run now correspond to a single token in the second run.

The relationship generation engine 270 may also alter a database using the stitched, normalized genealogical records. For example, a cluster database, a genealogical tree database, and/or a database such as a graph database, may be modified using the data. In some embodiments, the stitched data form new edges between nodes, e.g., between a node representing a person and a node representing or affiliated with an organization, such as a historical entity, and/or between the node representing the person and a node representing another person associated with the historical entity. In other embodiments, the stitched data form clusters of nodes from distinct data, records, and/or collections, e.g., between a node representing a person as determined from the normalized genealogical records and between a node representing a person in an existing genealogical tree.

Continuing with reference to FIG. 4, in some embodiments, process 400 can include identifying a life-event record that is commonly associated with a subset of clusters (step 450). The life-event record indicates that a plurality of deceased individuals are connected through a non-familial relationship in a life event documented by the life-event record. For example, the life event may be an enlistment in a military unit and the life-event record may be a military record. In another example, the life-event record may be a Census record and the life event may be living in a certain neighborhood. The relationship generation engine 270 identifies clusters that are commonly associated with the Census record, such as individuals who lived in the same neighborhood in a historical time period (e.g., 1900). In yet another yet, the life-event record may be a historical photo of an event such as a wedding. The relationship generation engine 270 may identify the guests who attended the wedding. The identification of those individuals may be through a non-familial relationship, but in various embodiments, this does not preclude that two or more individuals identified had blood relationship. For example, two relatives may happen to be enlisted in the same military unit. In addition, the relationship generation engine 270 may both non-familial and familial relationships in a database.

Continuing with reference to FIG. 4, in some embodiments, process 400 can include causing a graphical user interface to display a representation of a historical network among the plurality of deceased individuals that are connected through the non-familial relationship in the life event (step 460). The historical network may display the relationships as a list, a mesh, a tree or another suitable topology to illustrate the interrelationships among the individuals in the network. While the historical network typically includes at least one deceased individual, the historical network may also include present individuals and users of the computing server 130. Further examples of the results presented in a graphical user interface are shown in FIG. 5 through FIG. 10B. For example, if the life event is an enlistment to a military unit, the representation of the historical network indicates that the plurality of deceased individuals were in the military unit. The graphical user interface may also display the roles of one or more deceased individuals in the non-familial relationship, such as the rank or title in a military unit. The historical network may represent a historical organization. The relationship generation engine 270 may also determine the profile of a historical organization. The profile includes information from one or more genealogical records that are stitched to the subset of clusters that constitute the historical network.

In some embodiments, the historical network may also connect historical individuals with present-day individuals. For example, the relationship generation engine 270 may connect a deceased individual in the historical network to a family tree. The family tree includes one or more descendants of the deceased individual. The graphical user interface may display the family tree in response to a user selecting the deceased individual in the historical network. For example, the graphical user interface may indicate that the deceased individual in a historical network is an ancestor of a known user of the computing server 130. A user may expand the profile of the deceased individual to examine the family tree. In some embodiments, the relationship generation engine 270 may also identify two or more users of the computing server 130 are descendants of various deceased individuals in the historical network. In some cases, two of the users may be connected, such as being connected in a family tree or being friends in the computing server 130. The computing server 130 may provide notifications to the two users that they have a non-familial relationship through ancestors in the historical network. For example, the computing server 130 may notify two connected users that the great-grandfathers of both users were in the same military unit, lived in the same community, or attended the same historical event.

Turning to FIG. 5 through FIG. 9C, user interfaces 500, 600, 700, 800, and 900 illustrating a historical social network according to embodiments are shown and described. The user interface 500 of FIG. 5 may be directed to a particular historical event, as indicated by a label or headline 501. For example, the user interface 500 may direct a historical social network user to a profile or page for the Battle of Gettysburg. The user interface 500 may include one or more sections 502 through which a user may navigate to derive information, such as an overview of the event, organizations such as military units, e.g., regiments, involved therein, videos associated with the event, maps of the event, etc. The sections 502 may include one or more indicia 503 that notify a user of new, unexplored, and/or pertinent content. A section 504 may be populated with information explaining the event.

It will be understood that while military units, including regiments and companies, including those specific to the American Civil War, are described herein, any suitable organization and/or historical phenomenon may be similarly explored using historical social networks of the disclosure. Other wars, historical events, and types of human organizations such as neighborhoods, cities, congregations, professional or work organizations, civic leagues, or otherwise, may be visualized, explored, generated, transformed, and otherwise presented according to embodiments of the disclosure.

A search modality 505 may be provided in any suitable location or part of the user interface 500, and allows a user to search for, e.g., a particular organization involved in the event. A user who is aware or wishes to confirm that their great-great-grandfather fought in the Battle of Gettysburg, for instance, may search for a regiment associated with their great-great-grandfather to confirm whether said regiment was involved in the battle. A side panel 506 displaying high-level facts or references regarding the event may be arranged in any suitable part of the user interface 500. Upon searching for a particular regiment, such as the Maine $17^{th}$ Volunteer Infantry, the user may be guided to a regiment-specific user interface 600.

Turning to FIG. 6, a user interface 600 includes a label or headline 601 identifying an organization, such as a military unit, e.g., a regiment in the American Civil War. The user interface 600 may include one or more sections 602 through which the user may navigate including an overview, timeline, companies, soldiers, images, or otherwise. One or more of the sections 602 may include a body portion 604 in which information pertinent to the section may be displayed, such as lists, tables, descriptions, images, videos, etc. A search modality 605 may be provided in any suitable location allowing the user to search for, e.g., an individual soldier associated with the regiment, or an individual member of any suitable organization.

Additional sections, such as a side panel 606, or a body section 607, may be provided to display other information as suitable. In the case of a military unit, field officers, notable battles, timelines, commander lists, company lists, and other information may be provided as suitable. This may advantageously allow a user to explore, on a high level and/or any suitable or desired level of granularity, available information about the organization. Thus a user exploring the Maine $17^{th}$ Volunteer Infantry may discern and/or easily navigate to a list of companies, commanders, officers, battles, timelines, and other data associated therewith. This can allow a user searching for, e.g., a particular ancestor or another person of interest, to view, gather, or otherwise receive information that provides context and meaning about the ancestor or person of interest's life, experiences, and/or associations.

Turning to FIG. 7, a user interface 700 corresponding to another embodiment of a historical social network is shown and described. The user interface 700 corresponds to a yet-further level of granularity relative to the user interfaces 500, 600, and may correspond to a particular company of a regiment, e.g., a sub-unit of an organization. That is, the user interface 700 may correspond to a particular company as opposed to a regiment, which comprises a plurality of companies. A user may navigate to the user interface 700 from a link embedded in or otherwise accessible through the user interface 600, for example.

The user interface 700 includes, in some embodiments, a label or headline 701 identifying an organization, such as a military unit, e.g., a particular company of a regiment in the American Civil War. The user interface 700 may include one or more sections 702 through which the user may navigate including an overview, timeline, soldiers, images, or otherwise. One or more of the sections 702 may include a body portion 704 in which information pertinent to the section may be displayed, such as lists, tables, descriptions, images, videos, etc. A search modality 705 may be provided in any suitable location allowing the user to search for, e.g., an individual soldier associated with the company, or an individual member of any suitable organization.

Additional sections such as a side bar 706 or a body portion 707 may be arranged for displaying other suitable information, such as company leaders, notable soldiers, notable battles, company facts such as casualties, locations, and maps, etc. For example, a map of a home state for the company with accompanying enlistment locations and associated soldiers may be provided. A section 708 allows a user to navigate back to a previous user interface from or through which the user arrived at the user interface 700.

Figure 8:
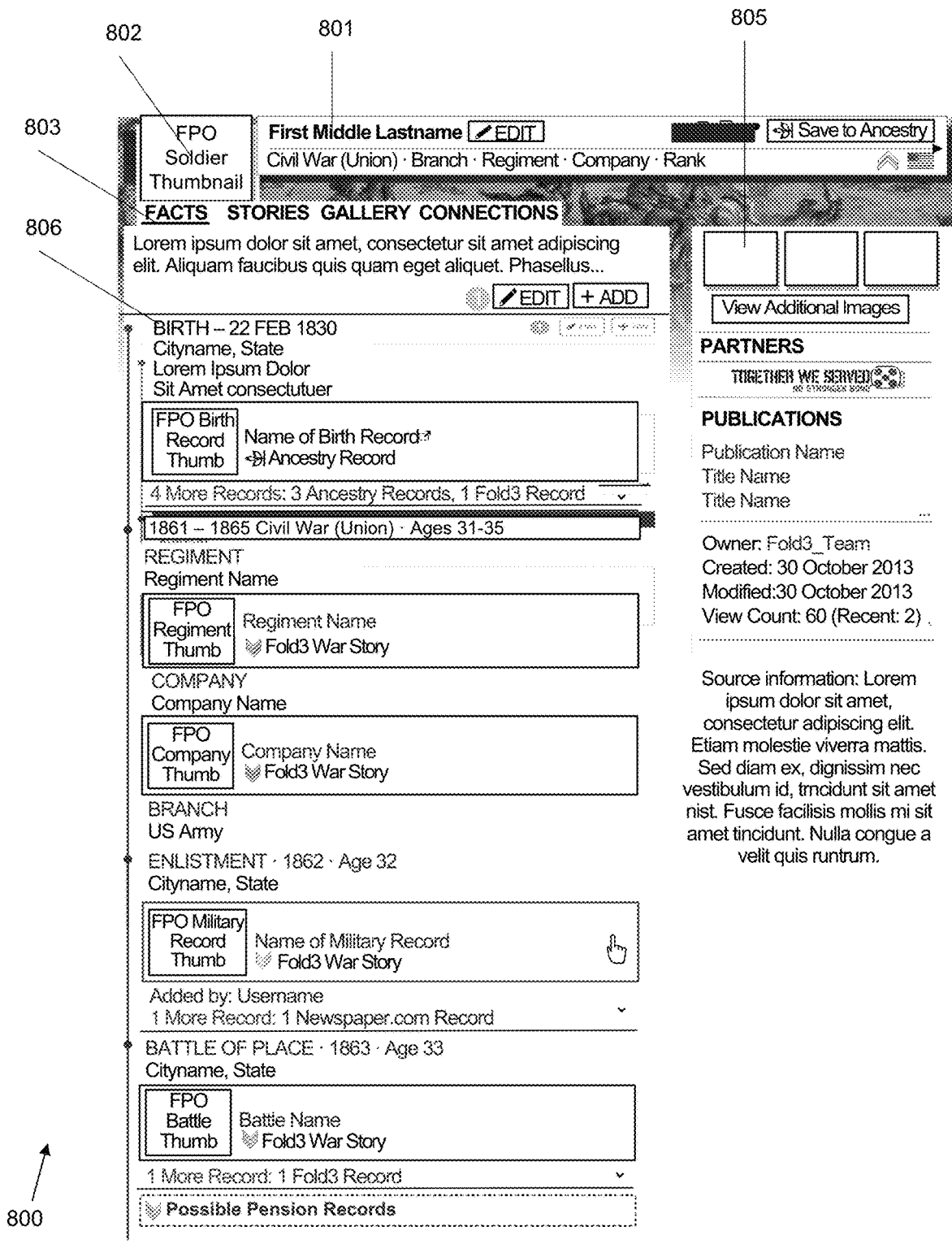
FIG. 8 illustrates a user interface of a historical social network according to another embodiment of the present disclosure.

Turning to FIG. 8, a user interface 800 for an individual is shown and described. The user interface 800 may be directed to a soldier of a company or regiment on the historical social network. The user interface 800 may include a headline or label 801 identifying, e.g., the soldier's name, and a profile image 802, which may be automatically determined. One or more sections 803, such as facts, stories, galleries, and connections, may be provided. Additional sections such as a link section 805 may provide additional resources for further information, and a timeline section 806 may provide a timeline of accumulated information about the individual, such as birth and death location and dates, burial information, and information about participation in a particular historical phenomenon, organization, or otherwise. For example, the timeline section 806 may include information about the organization in which the individual participated. In the example of a military unit such as a regiment and company, the timeline section 806 may include information about enlistment date, origin of the regiment, branch of the military, battles in which the regiment was involved, etc.

Turning now to FIGS. 9A-9C, a user interface 900 for an individual according to another embodiment is disclosed. The user interface 900 allows a user to explore a person in the context of their membership in a historical social network. The user interface 900 includes a headline or label 901 identifying the person by name and a profile image 902 identifying the person by image. The image and name may be automatically determined and/or may be selected or edited by a user. The profile of the user interface 900 includes one or more sections 903 for exploring, e.g., facts, stories, gallery, and connections of the person, with a timeline 906 and a side panel 905 populated with data normalized and stitched as described herein. For example, the side panel 905 may include a "supporting records" and/or a genealogical trees section 907, which link or navigate a user to stitched records with additional or supporting data and to genealogical trees containing the person of interest and/or associated persons, respectively. These may be obtained from the stitched tree database, the genealogical tree database, or the database 110.

Turning now to FIG. 9B, a connections tab or section 903 is highlighted in the user interface 950, wherein a section 951 is populated automatically. The section 951 includes one or more records retrieved, transformed, and/or selected according to the approach of FIG. 1. The section 951 may also detail a name of a record 952, an event 953 (e.g., life event) to which the record pertains, a title 954 of the record, and a source 955 of the record. Additional sections 960 may pertain to memorials, associated persons' profiles, etc.

Turning now to FIG. 9C, a user interface 975 includes a window 976 displayed in response to a user selection of an add button or option. The user interface 976 allows the user to add a fact, record, or other data, such as a birth date, including a source or a relationship, to a profile for a person, such as a historical person. This advantageously facilitates the addition of information not already contained in the database 110 and allows for access to the information by clustered-together persons and organizations.

Figure 10A:
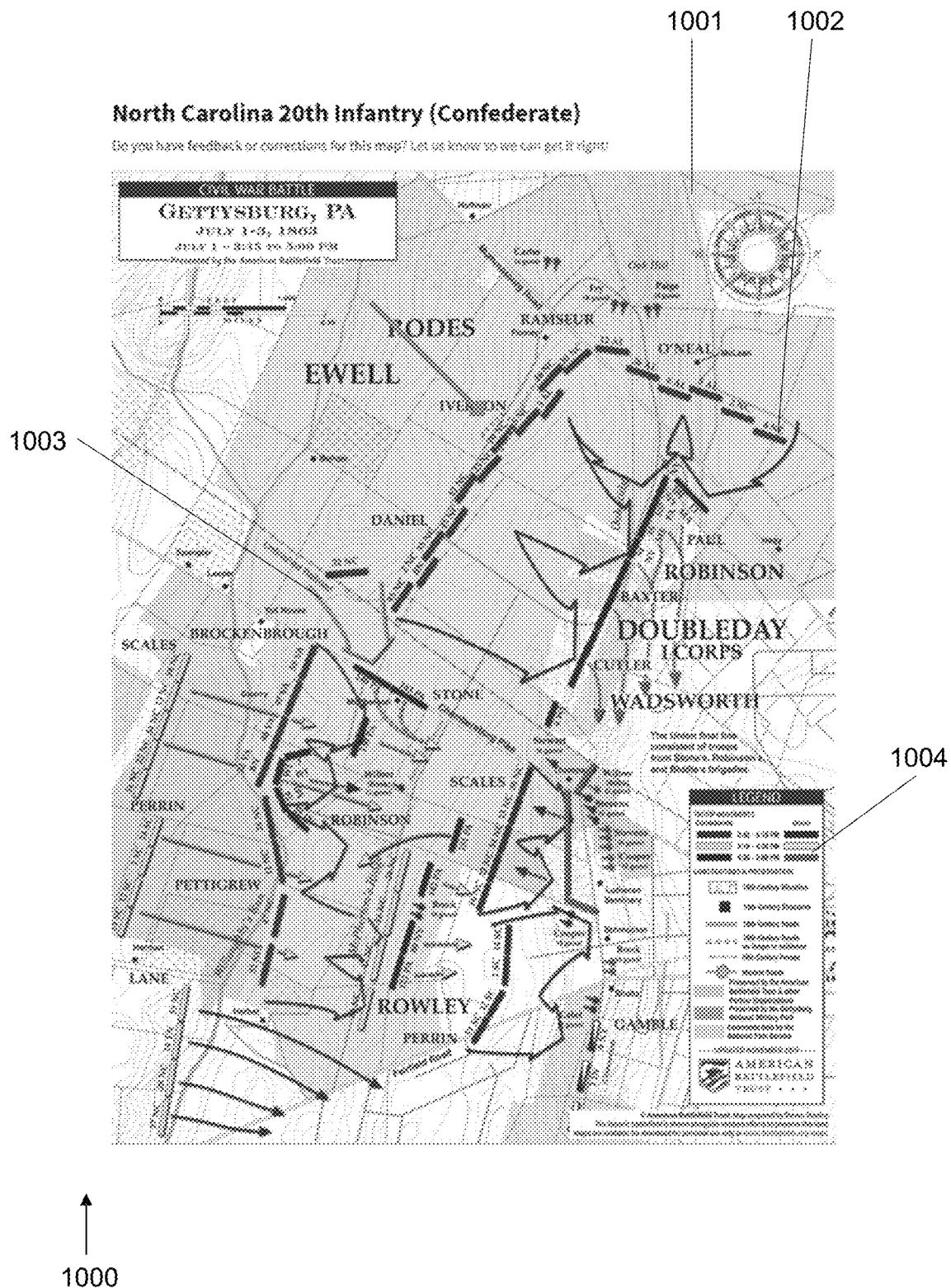
FIG. 10A illustrates a user interface of a historical social network, in accordance with some embodiments.

Turning now to FIG. 10A-10B, an interactive map 1000 generated according to embodiments is shown. The interactive map 1000 includes a base map 1002 and an interactive layer 1004 with a plurality of components pertaining to identified units. The identified units may be companies/regiments that participated in a battle, e.g., the Battle of Gettysburg. Using the transformed data obtained by automatically scraping contextual information sources as described above, individual unit participation in particular events, such as battles, can be obtained, transformed, and accessed by a user visually. As seen in FIG. 10A, a map 1000 of a particular timeframe within July 1 (day one) of the Battle of Gettysburg.

The map 1000 includes a base map 1001 overlaid with regiment components 1002, which may take a shape such as solid-color bars or rectangles, representing individual units, and movement components 1003, taking the form of arrows, representing the movement of units generally. The regiment components 1002 and the movement components 1003 may be color coded as shown in legend 1004 to depict the time. A user may click on or hover over one or more of the regiment components 1002 and/or the movement components 1003 to see more detailed information pertaining to the component and/or to link directly to a profile page or other information pertaining to the component.

FIG. 10B shows an administrator tool 1050, taking the form of a user interface, which may be configured to allow for receiving the map 1000 and linking the map to individual pages of a historical social network generated according to embodiments of the disclosure. For example, the administrator tool 1050 may facilitate a user drawing or otherwise setting a bounding box 1052 on an appropriate location of an underlying map 1051. A menu 1053 allows for selecting a regiment or other organization to assign to the bounding box such that, upon hovering over and/or clicking thereon, a user may link directly to the corresponding profile or page.

The menu 1053 may populate automatically based on the profiles or pages of regiments/organizations in the historical social network. The bar 1056 displays a name of the selected regiment/organization. The administrator tool advantageously facilitates the automatic import of organizations within a historical social network such that a map or other interface can be easily annotated therewith. This streamlines the process of providing interactive information to users. In some embodiments, users may supply the names or other details pertaining to particular organizations through the tool 1050, thereby facilitating the "crowdsourcing" of information through the historical social network.

Computing Machine Architecture

Figure 11:
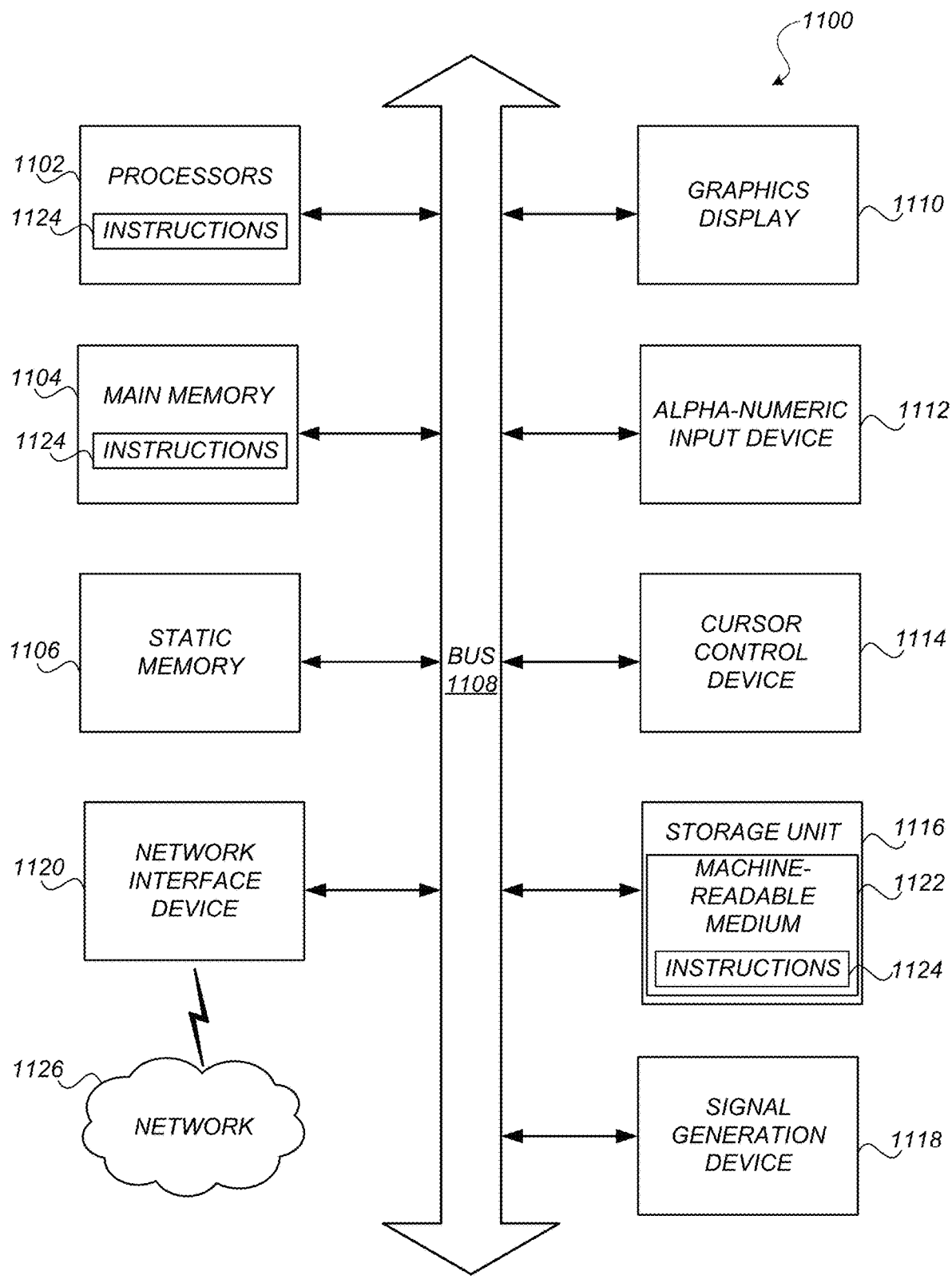
FIG. 11 is a block diagram of an example computing device, in accordance with some embodiments.

FIG. 11 is a block diagram illustrating components of an example computing machine that is capable of reading instructions from a computer-readable medium and execute them in a processor (or controller). A computer described herein may include a single computing machine shown in FIG. 11, a virtual machine, a distributed computing system that includes multiple nodes of computing machines shown in FIG. 11, or any other suitable arrangement of computing devices.

By way of example, FIG. 11 shows a diagrammatic representation of a computing machine in the example form of a computer system 1100 within which instructions 1124 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 11 may correspond to any software, hardware, or combined components shown in FIGS. 1 and 2, including but not limited to, the client device 110, the computing server 130, and various engines, interfaces, terminals, and machines shown in FIG. 2. While FIG. 11 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1124 that specify actions to be taken by that machine. Further, while only a single machine is illustrated, the term "machine" and "computer" may also be taken to include any collection of machines that individually or jointly execute instructions 1124 to perform any one or more of the methodologies discussed herein.

The example computer system 1100 includes one or more processors 1102 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1100 may also include a memory 1104 that store computer code including instructions 1124 that may cause the processors 1102 to perform certain actions when the instructions are executed, directly or indirectly by the processors 1102. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1102 and reduces the space required for the memory 1104. For example, the database processing techniques and machine learning methods described herein reduce the complexity of the computation of the processors 1102 by applying one or more novel techniques that simplify the steps in training, reaching convergence, and generating results of the processors 1102. The algorithms described herein also reduces the size of the models and datasets to reduce the storage space requirement for memory 1104.

The performance of certain operations may be distributed among more than one processor, not only residing within a single machine, but deployed across a number of machines. In some example embodiments, the one or more processors or processor-implemented modules may be located in a single geographic location (e.g., within a home environment, an office environment, or a server farm). In other example embodiments, one or more processors or processor-implemented modules may be distributed across a number of geographic locations. Even though in the specification or the claims may refer some processes to be performed by a processor, this should be construed to include a joint operation of multiple distributed processors.

The computer system 1100 may include a main memory 1104, and a static memory 1106, which are configured to communicate with each other via a bus 1108. The computer system 1100 may further include a graphics display unit 1110 (e.g., a plasma display panel (PDP), a liquid crystal display (LCD), a projector, or a cathode ray tube (CRT)). The graphics display unit 1110, controlled by the processors 1102, displays a graphical user interface (GUI) to display one or more results and data generated by the processes described herein. The computer system 1100 may also include alphanumeric input device 1112 (e.g., a keyboard), a cursor control device 1114 (e.g., a mouse, a trackball, a joystick, a motion sensor, or other pointing instruments), a storage unit 1116 (a hard drive, a solid-state drive, a hybrid drive, a memory disk, etc.), a signal generation device 1118 (e.g., a speaker), and a network interface device 1120, which also are configured to communicate via the bus 1108.

The storage unit 1116 includes a computer-readable medium 1122 on which is stored instructions 1124 embodying any one or more of the methodologies or functions described herein. The instructions 1124 may also reside, completely or at least partially, within the main memory 1104 or within the processor 1102 (e.g., within a processor's cache memory) during execution thereof by the computer system 1100, the main memory 1104 and the processor 1102 also constituting computer-readable media. The instructions 1124 may be transmitted or received over a network 1126 via the network interface device 1120.

While computer-readable medium 1122 is shown in an example embodiment to be a single medium, the term "computer-readable medium" should be taken to include a single medium or multiple media (e.g., a centralized or distributed database, or associated caches and servers) able to store instructions (e.g., instructions 1124). The computer-readable medium may include any medium that is capable of storing instructions (e.g., instructions 1124) for execution by the processors (e.g., processors 1102) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

By providing a historical social networks system, method, and/or computer-program product, the problem of existing approaches to genealogical research and to social networking being insufficient and ill-suited to the challenge of understanding historical organizations and persons' association therewith is addressed. The historical social networks embodiments of the disclosure advantageously facilitate the retrieval, transformation, selection, and organization of data from, e.g., historical records and stitching/clustering thereof with other data to yield insights into historical organizations and persons' participation in and association therewith.

While certain some embodiments may be directed to military regiments and contextual data pertaining to conflicts, it will be appreciated that the disclosed embodiments are not limited thereto, but rather extend to any suitable organization, record source, and/or contextual information. For example, historical social networks may be built for schools using optical character recognition ("OCR") processed yearbooks to extract nodes or entities, and relationships drawn therebetween using contextual data from the yearbooks and other sources. Associations between students may be inferred based on mutual membership in clubs, teams, classes, etc.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed in the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2020, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2020, (4) U.S. Pat. No. 10,558,930, entitled "Local Genetic Ethnicity Determination System," granted on Feb. 11, 2020, (5) U.S. Pat. No. 10,114,922, entitled "Identifying Ancestral Relationships Using a Continuous Stream of Input," granted on Oct. 30, 2018, (6) U.S. Pat. No. 11,429,615, entitled "Linking Individual Datasets to a Database," granted on Aug. 30, 2022, (7) U.S. Pat. No. 10,692,587, entitled "Global Ancestry Determination System," granted on Jun. 23, 2020, and (8) U.S. Patent Application Publication No. US 2021/0034647, entitled "Clustering of Matched Segments to Determine Linkage of Dataset in a Database," published on Feb. 4, 2021.

What is claimed is:

1. A computer-implemented method, comprising:
receiving a plurality of genealogical records, at least a subset of the plurality of genealogical records being historical records of deceased individuals;
normalizing the plurality of genealogical records into normalized genealogical records, normalizing the plurality of genealogical records comprising converting a text string of at least one of the plurality of genealogical records into a standardized format;
stitching the normalized genealogical records into a plurality of clusters, each cluster estimated to be corresponding to an individual and comprising one or more genealogical records associated with the individual, wherein stitching the normalized genealogical records into the plurality of clusters comprises:
generating tokens representing the plurality of clusters in a plurality of stitch runs;
generating identifiers for the plurality of clusters, the identifiers being unique across the plurality of stitch runs and being different from the tokens, wherein an identifier uniquely represents the individual; and
linking a first token corresponding to a first stitch run and a second token corresponding to a second stitch run to the identifier that uniquely represents the individual;
generating a stitched tree comprising nodes that represent tree individuals, the nodes being connected via edges specifying relationships among the tree individuals, wherein at least one node represents a tree individual that has a cluster of normalized genealogical records that are estimated to be belong to the individual;
detecting, utilizing a relationship generation engine to process a database of genealogical records, a life-event record that is commonly associated with a subset of clusters, the life-event record indicating that a set of deceased individuals are connected through a non-familial relationship in a life event documented by the life-event record;
adding, to the stitched tree, edges to the nodes representing the set of deceased individuals, the added edges representing that the set of deceased individuals are connected through the non-familial relationship in the life event;
generating a historical network among the set of deceased individuals that are connected through the non-familial relationship in the life event, the historical network comprising the edges added to the nodes representing the set of deceased individuals and comprising one or more genealogical records that are stitched as part of the subset of clusters;
generating, within the historical network, a historical organization profile for a historical organization through which the non-familial relationship connects the set of deceased individuals; and
causing a graphical user interface to display a representation of the historical network comprising the historical organization profile.

2. The computer-implemented method of claim 1, wherein the plurality of genealogical records comprise genealogical records from a genealogical tree database, wherein stitching the normalized genealogical records comprises searching for related records from the genealogical tree database.

3. The computer-implemented method of claim 2, further comprising generating the historical organization profile to include information from the one or more genealogical records that are stitched as part of the subset of clusters, wherein the one or more genealogical records are navigable within the historical organization profile displayed in the graphical user interface.

4. The computer-implemented method of claim 1, further comprising:
assigning a first token for each cluster in a first plurality of clusters generated in a first stitch run, the first token for each cluster representing a set of genealogical records that are identified to be stitched as a cluster in the first stitch run;
assigning an identifier to each cluster in the plurality of clusters, the identifier being used by a genealogy server as the identifier of the individual corresponding to a respective cluster;
assigning a second token for each cluster in a second plurality of clusters generated in a second stitch run, the second token for each cluster representing a set of genealogical records that are identified to be stitched as a cluster in the second stitch run; and
matching the second token with the identifier.

5. The computer-implemented method of claim 1, wherein the life-event record is a record of a military unit and the life event is joining the military unit together, and wherein the representation of the historical network indicates that the set of deceased individuals were in the military unit.

6. The computer-implemented method of claim 1, further comprising: organizing the normalized genealogical records based on a database schema of a graph database.

7. The computer-implemented method of claim 1, further comprising:
generating, within the historical network, a sub-unit organization profile for a sub-unit of the historical organization through which the non-familial relationship connects the set of deceased individuals; and
causing the graphical user interface to display a representation of the sub-unit organization profile within the representation of the historical network.

8. The computer-implemented method of claim 1, further comprising:
extracting, from refined data obtained from at least one data source, contextual data comprising data pertaining to events relevant to the historical organization utilizing an extraction model; and
causing the graphical user interface to display the contextual data within the historical organization profile.

9. The computer-implemented method of claim 1, further comprising generating a plurality of sections within the historical organization profile through which a user may navigate to derive information within the graphical user interface.

10. The computer-implemented method of claim 1, further comprising:
generating, within the historical network, a plurality of member profiles for individual members of the historical organization through which the non-familial relationship connects the set of deceased individuals; and
causing the graphical user interface to display representations of the plurality of member profiles within the representation of the historical network.

11. The computer-implemented method of claim 1, further comprising: causing the graphical user interface to display roles of one or more deceased individuals in the non-familial relationship.

12. The computer-implemented method of claim 1, further comprising:
connecting at least one deceased individual in the set of deceased individuals in the historical network to a family tree, the family tree comprising one or more descendants of the at least one deceased individual; and
causing the graphical user interface to display the family tree in response to a user selecting the at least one deceased individual in the historical network.

13. The computer-implemented method of claim 1, further comprising:
determining that two users of a genealogy server are descendants of two deceased individuals in the historical network; and
causing the graphical user interface to send a notification indicating the two users are connected through the historical network.

14. A system, comprising:
a computing server comprising one or more processors and memory in communication with the one or more processors, the memory configured to store code comprising instructions, wherein the instructions, when executed by the one or more processors, cause the one or more processors to perform steps comprising:
receiving a plurality of genealogical records, at least a subset of the plurality of genealogical records being historical records of deceased individuals;
normalizing the plurality of genealogical records into normalized genealogical records, normalizing the plurality of genealogical records comprising converting a text string of at least one of the plurality of genealogical records into a standardized format;
stitching the normalized genealogical records into a plurality of clusters, each cluster estimated to be corresponding to an individual and comprising one or more genealogical records associated with the individual, wherein stitching the normalized genealogical records into the plurality of clusters comprises:
generating tokens representing the plurality of clusters in a plurality of stitch runs;
generating identifiers for the plurality of clusters, the identifiers being unique across the plurality of stitch runs and being different from the tokens, wherein an identifier uniquely represents the individual; and
linking a first token corresponding to a first stitch run and a second token corresponding to a second stitch run to the identifier that uniquely represents the individual;
generating a stitched tree comprising nodes that represent tree individuals, the nodes being connected via edges specifying relationships among the tree individuals, wherein at least one node represents a tree individual that has a cluster of normalized genealogical records that are estimated to be belong to the individual;
generating a stitched tree comprising nodes that represent tree individuals, the nodes being connected via edges specifying relationships among the tree individuals, wherein at least one node represents a tree individual that has a cluster of normalized genealogical records that are estimated to be belong to the individual;
detecting, utilizing a relationship generation engine to process a database of genealogical records, a life-event record that is commonly associated with a subset of clusters, the life-event record indicating that a set of deceased individuals are connected through a non-familial relationship in a life event documented by the life-event record;
adding, to the stitched tree, edges to the nodes representing the set of deceased individuals, the added edges representing that the set of deceased individuals are connected through the non-familial relationship in the life event;

generating a historical network among the set of deceased individuals that are connected through the non-familial relationship in the life event, the historical network comprising the edges added to the nodes representing the set of deceased individuals and comprising one or more genealogical records that are stitched as part of the subset of clusters;

generating, within the historical network, a historical organization profile for a historical organization through which the non-familial relationship connects the set of deceased individuals; and causing a graphical user interface to display a representation of the historical network comprising the historical organization profile.

15. The system of claim 14, wherein the steps further comprise:

assigning a first token for each cluster in a first plurality of clusters generated in a first stitch run, the first token for each cluster representing a set of genealogical records that are identified to be stitched as a cluster in the first stitch run;

assigning an identifier to each cluster in the plurality of clusters, the identifier being used by a genealogy server as the identifier of the individual corresponding to a particular cluster;

assigning a second token for each cluster in a second plurality of clusters generated in a second stitch run, the second token for each cluster representing a set of genealogical records that are identified to be stitched as a cluster in the second stitch run; and matching the second token with the identifier.

16. The system of claim 14, wherein the life-event record is a record of a military unit and the life event is joining the military unit together, and wherein the representation of the historical network indicates that the set of deceased individuals were in the military unit.

17. The system of claim 14, wherein the steps further comprise:

extracting, from refined data obtained from at least one data source, contextual data comprising data pertaining to events relevant to the historical organization utilizing an extraction model; and causing the graphical user interface to display the contextual data within the historical organization profile.

18. The system of claim 14, wherein the steps further comprise:

connecting at least one deceased individual in the set of deceased individuals in the historical network to a family tree, the family tree comprising one or more descendants of the at least one deceased individual; and causing the graphical user interface to display the family tree in response to a user selecting the at least one deceased individual in the historical network.

19. The system of claim 14, wherein the steps further comprise:

determining that two users of a genealogy server are descendants of two deceased individuals in the historical network; and causing the graphical user interface to send a notification indicating the two users are connected through the historical network.

20. A non-transitory computer readable medium configured to store code comprising instructions, wherein the instructions, when executed by one or more processors, cause the one or more processors to perform steps comprising:

receiving a plurality of genealogical records, at least a subset of the plurality of genealogical records being historical records of deceased individuals;

normalizing the plurality of genealogical records into normalized genealogical records, normalizing the plurality of genealogical records comprising converting a text string of at least one of the plurality of genealogical records into a standardized format;

stitching the normalized genealogical records into a plurality of clusters, each cluster estimated to be corresponding to an individual and comprising one or more genealogical records associated with the individual, wherein stitching the normalized genealogical records into the plurality of clusters comprises:

generating tokens representing the plurality of clusters in a plurality of stitch runs;

generating identifiers for the plurality of clusters, the identifiers being unique across the plurality of stitch runs and being different from the tokens, wherein an identifier uniquely represents the individual; and linking a first token corresponding to a first stitch run and a second token corresponding to a second stitch run to the identifier that uniquely represents the individual;

generating a stitched tree comprising nodes that represent tree individuals, the nodes being connected via edges specifying relationships among the tree individuals, wherein at least one node represents a tree individual that has a cluster of normalized genealogical records that are estimated to be belong to the individual;

determining, utilizing a relationship generation engine to process the plurality of clusters, a subset of clusters corresponding to contextual data defining a life event extracted from the plurality of genealogical records;

detecting a life-event record that is commonly associated with the subset of clusters determined utilizing the relationship generation engine, the life-event record indicating that a set of deceased individuals are connected through a non-familial relationship in a life event documented by the life-event record;

adding, to the stitched tree, edges to the nodes representing the set of deceased individuals, the added edges representing that the set of deceased individuals are connected through the non-familial relationship in the life event;

generating a historical network among the set of deceased individuals that are connected through the non-familial relationship in the life event, the historical network comprising the edges added to the nodes representing the set of deceased individuals and comprising one or more genealogical records that are stitched as part of the subset of clusters;

generating, within the historical network, a historical organization profile for a historical organization through which the non-familial relationship connects the set of deceased individuals; and causing a graphical user interface to display a representation of the historical network comprising the historical organization profile.

* * * * *